United States Patent
Ryan et al.

(10) Patent No.: US 6,964,274 B1
(45) Date of Patent: Nov. 15, 2005

(54) TUBAL STERILIZATION DEVICE HAVING EXPANDING ELECTRODES AND METHOD FOR PERFORMING STERILIZATION USING THE SAME

(75) Inventors: Thomas P. Ryan, Flemington, NJ (US); Roddi Simpson, Watchung, NJ (US); Vincenza Zaddem, Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/862,209

(22) Filed: Jun. 7, 2004

(51) Int. Cl.$^7$ ............................................. A61F 6/06
(52) U.S. Cl. ..................... 128/830; 128/831; 128/898; 600/29
(58) Field of Search ............................. 128/830–841, 128/898, 899, 885, 886, DIG. 25; 600/29–31; 606/41; 604/514, 515

(56) References Cited

U.S. PATENT DOCUMENTS

| | | | |
|---|---|---|---|
| 4,601,698 A * | 7/1986 | Moulding, Jr. ............... | 128/831 |
| 4,823,791 A | 4/1989 | D'Amelio et al. | |
| 4,834,091 A * | 5/1989 | Ott ............................... | 128/830 |
| 5,098,431 A | 3/1992 | Rydell | |
| 5,122,137 A | 6/1992 | Lennox | |
| 5,556,396 A | 9/1996 | Cohen et al. | |
| 5,979,446 A * | 11/1999 | Loy ............................. | 128/830 |
| 5,980,519 A * | 11/1999 | Hahnen et al. ................ | 606/41 |
| 6,001,095 A | 12/1999 | de la Rama et al. | |
| 6,066,139 A | 5/2000 | Ryan et al. | |
| 6,077,261 A | 6/2000 | Behl et al. | |
| 6,145,505 A * | 11/2000 | Nikolchev et al. .......... | 128/830 |
| 6,346,102 B1 | 2/2002 | Harrington et al. | |
| 6,352,549 B1 | 3/2002 | Everett | |
| 6,357,443 B1 * | 3/2002 | Loy ............................. | 128/830 |
| 6,378,524 B1 | 4/2002 | Jones | |
| 6,432,116 B1 | 8/2002 | Callister et al. | |
| 6,485,466 B2 | 11/2002 | Hamilton | |
| 6,488,678 B2 | 12/2002 | Sherman | |
| 6,871,650 B1 * | 3/2005 | Nikolchev et al. .......... | 128/830 |
| 2002/0020417 A1 | 2/2002 | Nikolchev et al. | |
| 2002/0100480 A1 | 8/2002 | Nikolchev et al. | |
| 2002/0148476 A1 | 10/2002 | Farley et al. | |

* cited by examiner

*Primary Examiner*—Fadi H. Dahbour

(57) ABSTRACT

A sterilization device which causes occlusion to the fallopian tubes of a patient is designed to be trancervically positioned in the intramural portion of the tube without perforating the tube. The device includes a flexible hollow catheter having an interior passageway, a distal end for insertion trancervically into a patient, and a proximal end opposite the distal end for grasping and manipulation by a physician. The device further includes a pair of diametrically opposed electrodes, each being movably mounted on the distal end of the catheter and radially movable with respect to the distal end. The electrodes are elongated axially and arcuate transversely and are expandable from a closed state, which defines the distal end of the catheter with a reduced diameter for proper transcervical delivery and placement in the fallopian tube of a patient, and an open state, where the electrodes are separated from one another a greater distance than when they are in the closed state, to define the distal end of the catheter with an enlarged diameter. In the expanded state, the diametrically opposed electrodes stretch the tissue of the fallopian tube to reduce blood flow and to help localize heating of the surrounding tissue. The electrodes are provided with RF (radio frequency) energy in their expanded state to heat the tissue of the fallopian tube which they contact. A temperature sensor situated at the distal end of the catheter measures the temperature of the heated tissue. The RF energy provided to the electrodes is controlled to ensure that the tissue is not overheated.

17 Claims, 19 Drawing Sheets

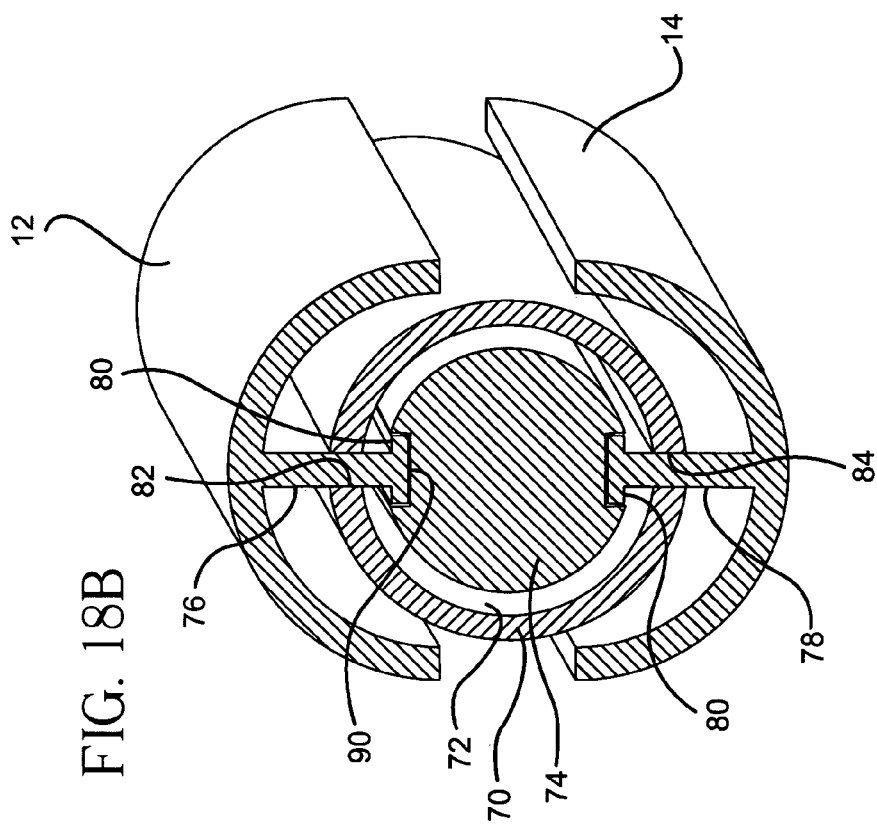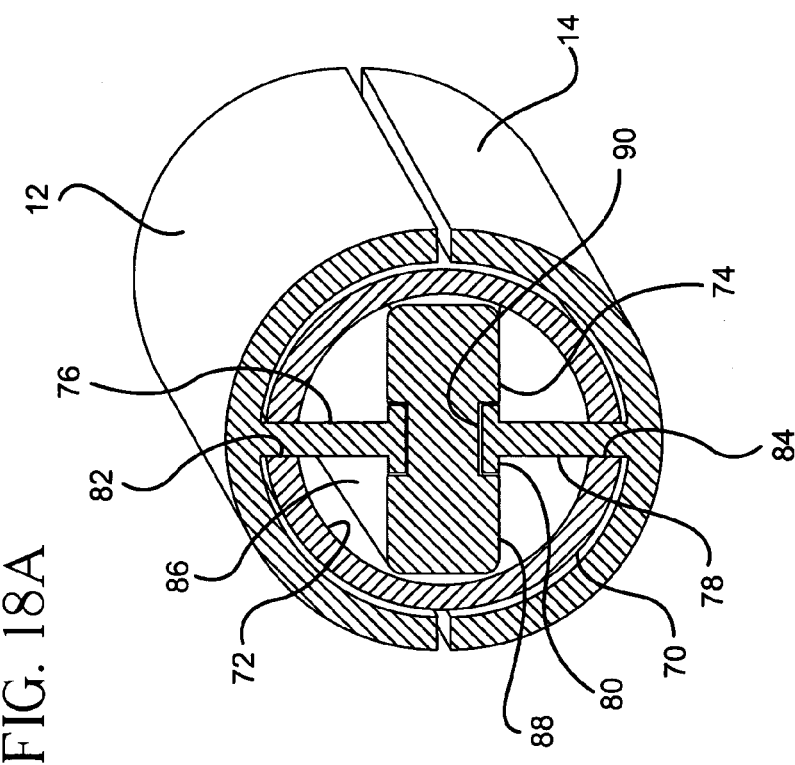
FIG. 18B
FIG. 18A

TUBAL STERILIZATION DEVICE HAVING EXPANDING ELECTRODES AND METHOD FOR PERFORMING STERILIZATION USING THE SAME

BACKGROUND OF THE INVENTION

1. Field of the Invention

The present invention generally relates to devices for occluding a body lumen, and more specifically relates to a permanent contraceptive or sterilization device for occluding a reproductive tract or lumen. Even more particularly, the present invention relates to a device which causes sterility in women by occluding the female reproductive fallopian tubes using RF (radio frequency) energy.

2. Description of the Prior Art

Many methods of female sterilization have been investigated. One method is surgical tubal ligation, which is a procedure in which the uterine tubules are tied and cut or clamped through an incision made through the wall of the abdomen. Tubal ligation done with a laparotomy requires a surgical incision in the abdomen under general anesthesia. Drawbacks of this procedure necessarily include the risks inherent with anesthesia and the permanent scar formation at the site of the incision. Another technique involves transcervically instilling the sclerosing agent quinacrine into the uterus and fallopian tubes to create a permanent closure of the fallopian tubes. Drawbacks of this procedure include the need of repeat applications and a significant level of side effects.

A further procedure involves transcervically injecting a curable elastomeric composition such as silicone into the fallopian tubes in an amount sufficient to fill the portion of the oviduct adjacent the uterus, which composition is allowed to cure and solidify to non-surgically block the tube. This technique is time consuming and requires a high level of technical skill.

There are also permanent contraceptive or sterilization devices which are transcervically delivered and mechanically anchored within the fallopian tubes and which promote tissue in growth into the device and scar tissue formation which eventually totally occludes each fallopian tube. Such a device is disclosed in U.S. Pat. No. 6,432,116 (Callister et al.) and published U.S. patent application Ser. No. 09/912,067 (Nikolchev et al.).

Sterilization has also been performed using RF (radio frequency) energy. As disclosed in U.S. Pat. No. 5,556,396 (Cohen et al.), an electrically energizable electrode is advanced into the fallopian tube and energized to thermally damage the fallopian tube, thereby causing enough scarring of the fallopian tube to permanent occlude it. Further sterilization devices using RF energy are disclosed in U.S. Pat. No. 6,066,139 (Ryan et al.) and U.S. Pat. No. 6,346,102 (Harrington et al.).

OBJECTS AND SUMMARY OF THE INVENTION

It is an object of the present invention to provide a transcervically deliverable tubal sterilization device which obviates the need for surgery.

It is another object of the present invention to provide a sterilization device which is flexible to facilitate placement in the fallopian tube transcervically, which placement may be guided visually using a hysteroscope.

It is still another object of the present invention to provide a tubal sterilization device which uses commonly accepted RF (radio frequency) energy.

It is a further object of the present invention to provide a tubal sterilization device employing a catheter which only enters the fallopian tube in the wall of the uterus, thus reducing the risk of perforation.

It is yet a further object of the present invention to provide a tubal sterilization device which effectively causes occlusion of the fallopian tube by heating the intramural portion of the tube, thereby being safer and reducing any risk of heating adjacent structures or organs, such as the bladder or bowel.

It is still a further object of the present invention to provide a tubal sterilization device which expands when properly positioned within the fallopian tube to reduce blood flow in the adjacent tissue, thereby helping to localize the heating.

It is still another object of the present invention to provide a sterilization device for sterilizing human females, which device employs bipolar RF energy to avoid stray currents and unnecessary heating.

It is yet a further object of the present invention to provide a tubal sterilization device which applies RF energy to heat the fallopian tubal wall and which monitors the temperature of the tissue to ensure a reproducible and safe heating of the tissue.

It is a further object of the present invention to provide a tubal sterilization device in which no foreign object remains in the body after the sterilization procedure, which might otherwise cause a reaction or affect imaging of the patient.

It is yet another object of the present invention to provide a tubal sterilization device which causes occlusion of the fallopian tube by natural healing rather than by foreign body placement, which foreign body may be displaced by peristalsis.

It is still another object of the present invention to provide a method for performing sterilization using a sterilization device formed in accordance with the present invention.

In accordance with one form of the present invention, a sterilization device which causes occlusion to the fallopian tubes is designed to be transcervically positioned in the intramural portion of the tube without perforating the tube. The device preferably includes a hollow, at least partially flexible, catheter having an interior passageway. The catheter has a first end (or patient end) for insertion transcervically into a patient, and a second end opposite the first end for grasping and manipulation by a physician. The device further includes a pair of diametrically opposed electrodes, each being movably mounted on the catheter at the first end. The electrodes are radially movable with respect to the first end of the catheter so that they may reside in either a first, closed state, thereby defining the patient end of the catheter with a reduced diameter for proper transcervical delivery and placement in the tubal osteum (and, in particular, the intramural portion) of the fallopian tube, and are expandable to a second, open position to define the patient end with an enlarged diameter. In this second, expanded state, the diametrically opposed electrodes stretch the tissue of the fallopian tube and reduce blood flow to help localize heating of the surrounding tissue.

The electrodes are responsive to RF (radio frequency) energy provided by, generically, an RF signal generator. The electrodes are activated with about five watts of RF energy, each electrode being separated from the other so that each electrode may be oppositely polarized to allow the application of bipolar energy. The device may include a thermistor, RTD, thermocouple, fiber optic sensor or other temperature sensitive device to monitor the temperature of the surrounding tissue undergoing heating. An electrical signal indicative of the tissue temperature is provided to and received by a control circuit. The control circuit thus monitors the heat of the surrounding tissue and compares it to a desired temperature range, for example, 95°–105° Celsius, and generates a control signal to the RF signal generator to adjust the power of the RF energy applied by the generator to the electrodes in a continual feedback arrangement.

After the surrounding tissue is heated to a desired temperature for a desired period of time, no further RF energy is applied by the generator to the electrodes, and the electrodes are retracted to their first, closed state to, again, provide the patient tip of the catheter with a reduced diameter. The catheter is then withdrawn from the patient.

The tubal sterilization device of the present invention is not intended to char or burn the walls of the fallopian tube. Rather, it is a healing process which ultimately occludes the treated fallopian tube. The initial response of the heating of the fallopian tube is an inflammatory response that then begins to close the tube. Over time, the tissue fibroses, and the lumen closes or is obliterated. It may require from two to four weeks before complete tubal occlusion occurs.

These and other objects, features and advantages of the present invention will be apparent from the following detailed description of illustrative embodiments thereof, which is to be read in connection with the accompanying drawing.

BRIEF DESCRIPTION OF THE DRAWING

FIG. 18A is a partial cross-sectional and isometric view of an illustrative portion of the tubal sterilization device shown in FIG. 16, taken along line 18A—18A of FIG. 16.

FIG. 18B is a partial cross-sectional and isometric view of an illustrative portion of the tubal sterilization device shown in FIG. 17, taken along line 18B—18B of FIG. 17.

DETAILED DESCRIPTION OF THE PREFERRED EMBODIMENTS

Figure 1:
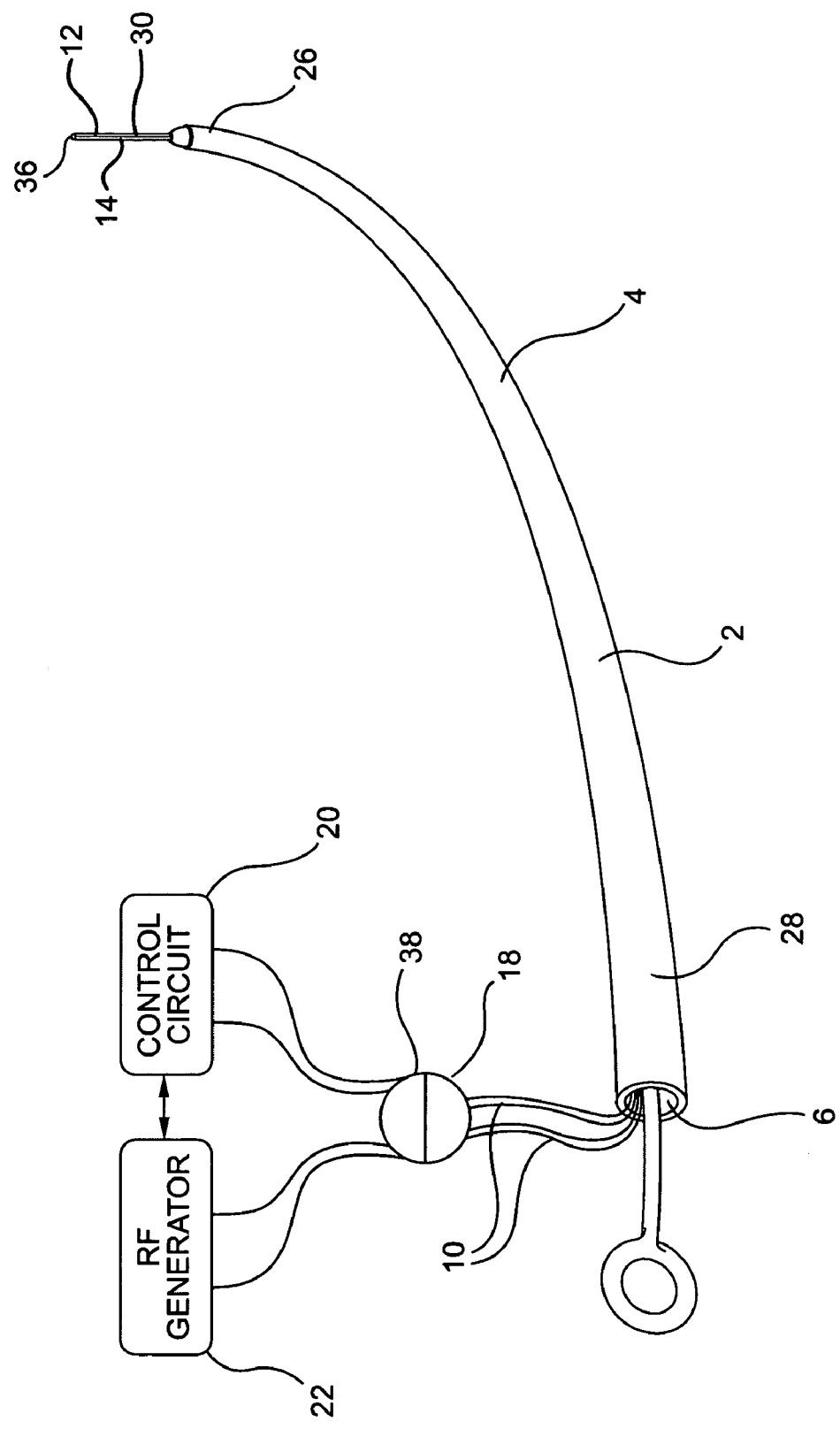
FIG. 1 is an isometric view of the general configuration of the tubal sterilization device formed in accordance with the present invention.
Figure 2:
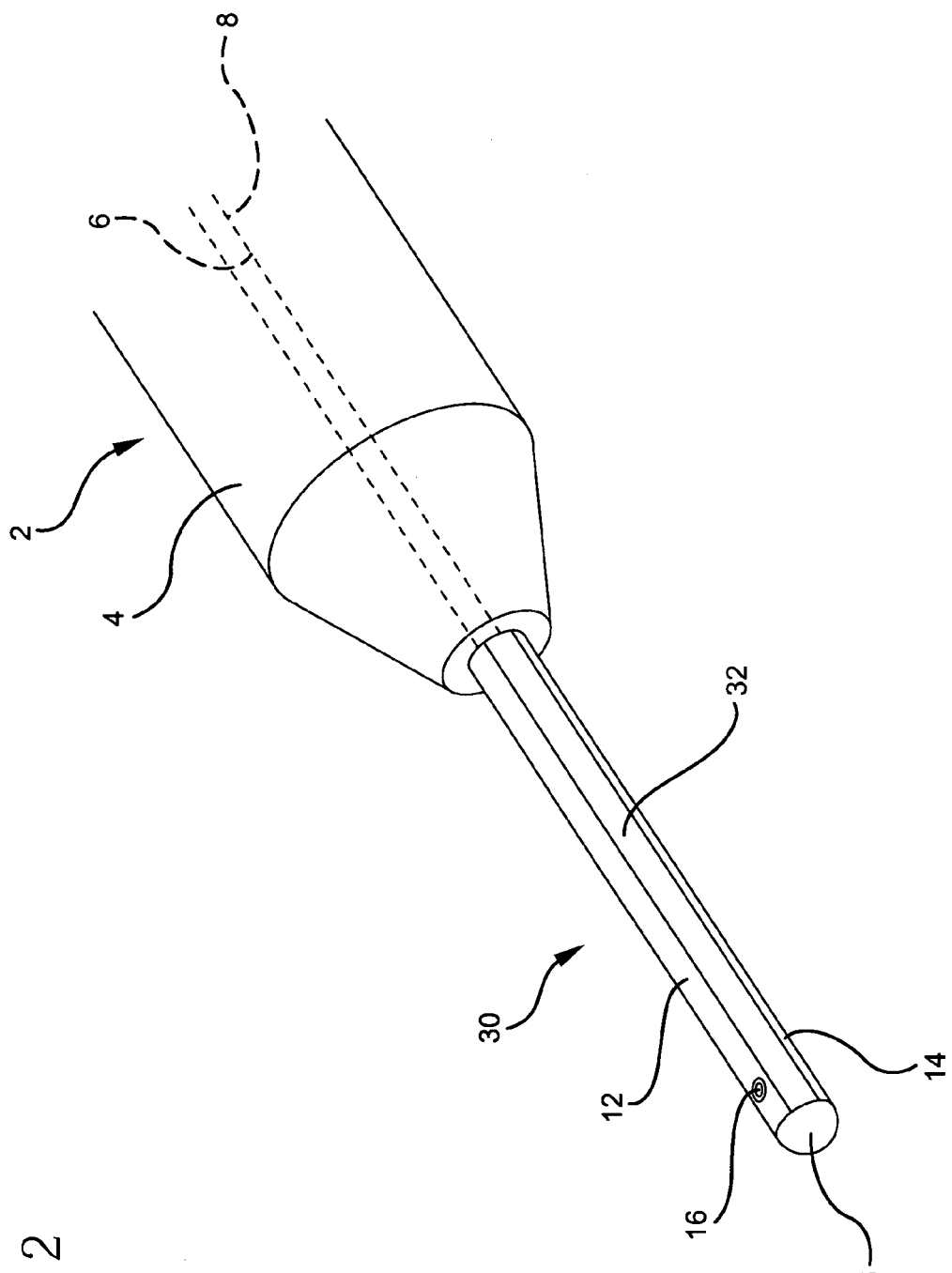
FIG. 2 is an isometric view of a tubal sterilization device formed in accordance with one form of the present invention.
Figure 3:
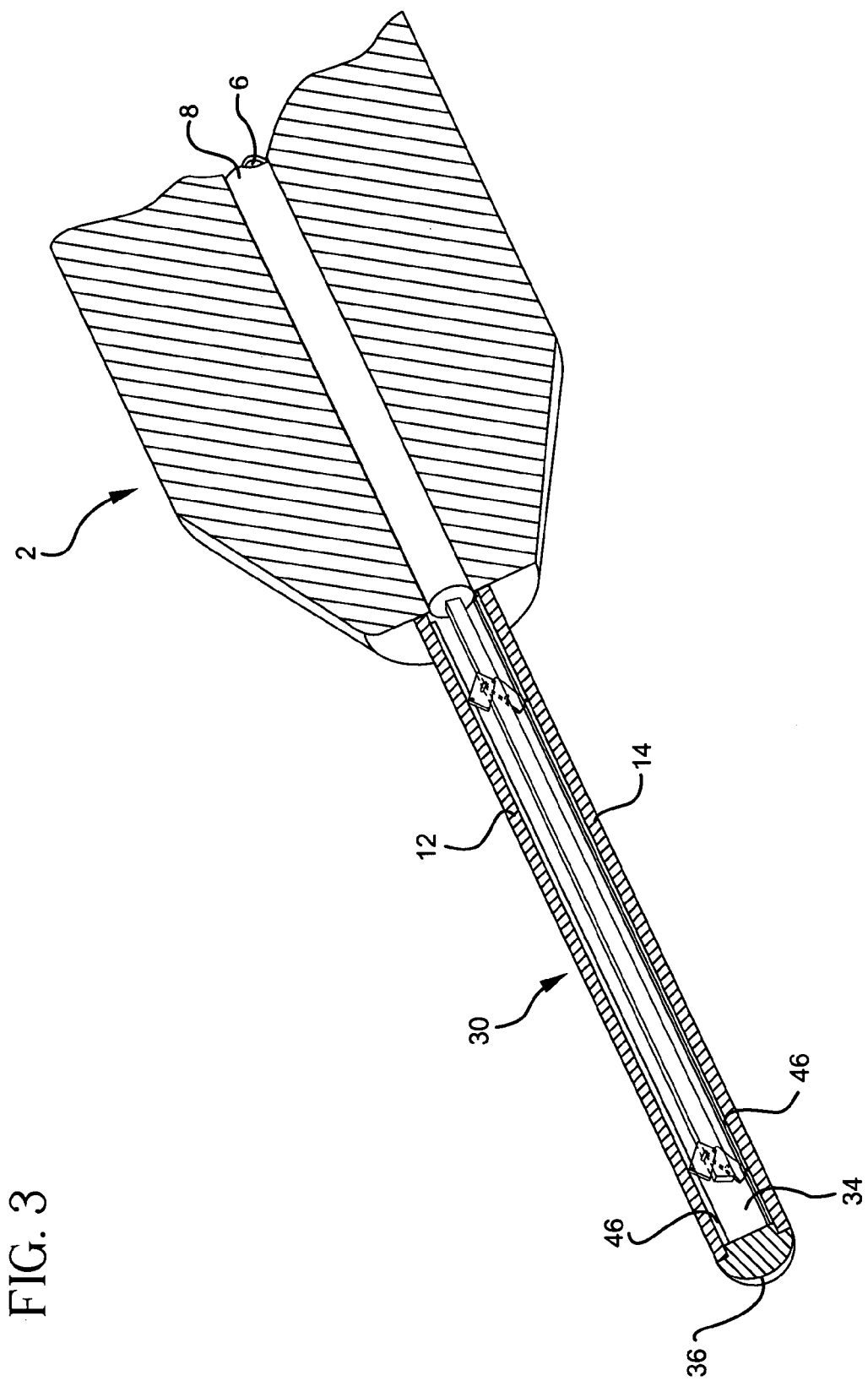
FIG. 3 is a cross-sectional view of the tubal sterilization device shown in FIG. 2, taken along line 3—3 of FIG. 2.

Several embodiments of a tubal sterilization device formed in accordance with the present invention are disclosed herein. In each embodiment, RF (radio frequency) energy is used to heat particular portions of the fallopian tube of a patient which, through the healing process, eventually occludes the fallopian tube to cause permanent contraception or sterilization. Each embodiment, as will be described, includes at least a pair of expandable electrodes which are electrically separated from each other in their expanded state to prevent their shorting so that a bipolar RF signal may be provided to the electrodes to cause heating of the surrounding tissue with which the electrodes come in contact.

In each of the embodiments of the present invention, the electrodes are initially in a first, closed position to facilitate the transcervical insertion of the device into the fallopian tube of the patient. When the device is positioned in a desired location within the fallopian tube, the physician manipulates the device to cause the electrodes to expand from its closed position to an second, enlarged diameter position, where the electrodes are even further separated from each other and exert pressure on the surrounding tissue of the fallopian tube. In this enlarged configuration, the sterilization device has the advantage of ensuring contact between the electrodes and the surrounding tissue, and the separated electrodes will stretch the tissue and reduce blood flow which will help localize the heating of the surrounding tissue when RF energy is applied to the electrodes. In addition, the electrodes will not be in contact while energy is applied since they have been deployed.

A temperature sensor, such as a thermistor, thermocouple, thermopile or the like, may be positioned on the tubal sterilization device to detect the temperature of the tissue heated by the electrodes. The temperature sensor provides a signal indicative of the temperature of the tissue to a control circuit, which may include a microprocessor or the like, which, in a feedback arrangement, monitors and responds to the temperature sensor signal and generates a control signal in response thereto, which control signal is provided to an RF signal generator, which provides the RF energy to the electrodes, to control the power of the RF signal provided to the electrodes by the generator.

For a more detailed explanation of a temperature sensor, an RF generator and a control circuit, for example, a microprocessor, reference is made to U.S. Pat. No. 6,066,139 (Ryan et al.), the disclosure of which is incorporated herein by reference.

The various embodiments of the tubal sterilization device formed in accordance with the present invention will now be described in detail in association with the particular figures of the drawing.

Initially referring to FIGS. 1–7 of the drawing, a tubal sterilization device formed in accordance with one form of the present invention is shown and will be described. The sterilization device basically includes a hollow catheter 2 which is an elongate member having an outer housing or cover 4 and which defines an interior passageway 6. As will be described in greater detail, the interior passageway 6 allows a push rod 8 to pass therethrough, as well as wires 10 or other electrical connections which are connected to the electrodes 12, 14 and the temperature sensor 16 at one end of the catheter 2 and which are further connected to an electrical connector 18 at the other end for connection to the control circuit 20 and RF energy signal generator 22.

More specifically, the catheter 2, or at least a portion thereof, is generally circular in cross-section and is particularly sized for transcervical insertion into a fallopian tube 24 of a patient. The catheter 2 has a first end 26, also referred to as the patient end 28, which is inserted transcervically into the patient, and a second end 28 opposite the first end 26 for grasping and manipulation by a physician. It is the first end of the catheter which is of primary interest in the present invention, as this is where the electrodes 12, 14 are located and the primary structure for moving the electrodes between the closed, unexpanded state and the open, expanded state, as will be described in greater detail.

Preferably, the first end 26 of the hollow catheter 2 is directed by the physician by his manipulation of the second end 14 so that it is placed through the cervix into the uterine cavity and, from there, it is moved to the tubal osteum, which is the entrance to the fallopian tube. There is a thick muscular wall in this initial segment of the tube called the intramural portion. This is the preferred placement of the patient end of the catheter. By staying in the intramural portion of the fallopian tube 24, use of the tubal sterilization device of the present invention will be safer and reduce any risk of heating adjacent structures such as the bladder or bowel. Placement and positioning of the catheter tip 26 of the tubal sterilization device may be directly visualized with a hysteroscope.

An electrode tip 30 is situated at the patient end 26 of the hollow catheter 2. The electrode tip 30 includes a first electrode 12 and a second electrode 14, each of which is formed of an electrically conductive material. Preferably, the first and second electrodes 12, 14 are situated diametrically opposite one another. The electrode tip 30 is generally cylindrical in shape, as mentioned above, and is defined by the opposite first and second electrodes 12, 14 and by electrode tip housing portions 32 interposed between facing adjacent side edges of the first and second electrodes 12, 14. Together, the electrode tip housing portions 32 and the first and second electrodes 12, 14 define a cylindrically-shaped outer wall of the electrode tip 30 and an interior chamber or cavity 34 situated radially inwardly of the electrodes 12, 14 and tip housing portions 32. The electrode tip housing portions 32, which together define the tip housing, are preferably made from an electrically non-conductive material, such as polyethylene.

The first and second electrodes 12, 14 are preferably elongated in the axial direction and arcuate or curved in the transverse direction. The electrode tip housing portions 32 are similarly elongate in the axial direction and arcuate in the transverse direction. Both the electrodes 12, 14 and the tip electrode housing portions 32 have similar radii to define together the outer wall of the cylindrical electrode tip 30.

The electrode tip 30 further includes a blunt tip 36 at its unsupported or free end, preferably in a hemispherical shape, to facilitate the introduction of patient end 26 of the catheter 2 into the fallopian tube 24 and to avoid perforation thereof. The blunt tip 36 is affixed to the axial free ends of the electrode tip housing portions 32.

As mentioned previously, the first and second electrodes 12, 14 are capable of moving radially on the electrode tip 30, which defines the first end or patient end 26 of the catheter 2. In their first, unexpanded state, the first and second electrodes 12, 14 define with the electrode tip housing portions 32 the generally cylindrical outer wall of the electrode tip 30. Thus, the first and second electrodes 12, 14 are spaced apart from each other a first distance when in the unexpanded state and provide the electrode tip, i.e., the first end 26 of the catheter 2, with a relatively small diameter that facilitates the insertion into and placement within the tubal osteum and intramural portion of the fallopian tube 24.

However, the first and second electrodes 12, 14 are expandable to a second, open state, where they are separated from each other by a second distance which is greater than the first distance and in which the first and second electrodes 12, 14 extend radially beyond the general cylindrical extent of the electrode tip 30 defined by the electrodes 12, 14 and electrode tip housing portions 32 when the electrodes are in the closed, unexpanded state. The preferred distance, i.e., the second distance, by which the first and second electrodes 12, 14 are separated in their expanded state is between about 0.5 millimeters and about 1.5 millimeters.

It is in the expanded state that the electrodes 12, 14 are used for heating the surrounding tissue of the fallopian tube 24 which they contact. The expanded electrodes stretch the tissue of the intramural segment of the fallopian tube 24 which has the effect of not only ensuring good contact with the surrounding tissue but also causing a reduced blood flow through the tissue to help localize its heating. In this expanded state, the electrodes 12, 14 are bipolarly energized with RF energy from an RF energy signal generator 22. The energy is provided on wires 10, flexible conductive runs formed on the interior wall of the catheter 2 or other electrical connections running axially through the interior passageway 6 of the hollow catheter 2 to which the electrodes 12, 14 are connected. A temperature sensor 16, such as a thermistor, thermocouple, thermopile or the like, may be insulatively mounted on one or both of the electrodes 12, 14 or on one or more of the electrode tip housing portions 32 and also connected by wires 10, flexible conductive runs or other connections which pass through the catheter passageway 6. Alternatively, the electrode wires 10 and temperature sensor wires 10 may be formed as part of the push rod 8. The electrode wires 10 and temperature sensor wires 10 are provided to a terminal connector 18, which is matable with another connector 38 that is electrically coupled to a control circuit 20, which may include a microprocessor, and to the RF signal generator 22.

The temperature sensor 16 measures the temperature of the tissue which is heated by the electrodes 12, 14 and generates an electrical signal indicative of that temperature, which electrical signal is received by the control circuit 20 and which signal is processed by the control circuit. The control circuit 20 thus monitors the temperature of the heated tissue and compares it to a desired range of temperatures to ensure that the tissue is not charred or burned. The control circuit 20, in turn, generates a control signal which is provided to the RF energy signal generator 22 to control the power of the RF signal provided to the electrodes 12, 14. Thus, the temperature sensor 16, control circuit 20, RF energy signal generator 22 and the electrodes 12, 14 define together a feedback loop so that only a controllable level of RF power is provided to the electrodes to prevent charring or overheating of the targeted area. Preferably, only sufficient energy is applied to the electrodes 12, 14 to result in tissue temperatures between about 95° Celsius and about 105° Celsius.

When the first and second electrodes 12, 14 are separated and positioned in their expanded state, they are activated with about 5 watts of RF energy and the heating takes place around and between the two active electrodes 12, 14. Power is adjusted to control the temperature and further to avoid steam formation and the resulting pressure waves. Heat is applied for a duration of preferably between about 0.5 minutes and about 5 minutes at a power setting of about 5 watts, and more preferably between about 1 minute and about 2 minutes at a power setting of about 5 watts.

After heat has been applied to the targeted area of the fallopian tube 24, the electrodes 12, 14 are deactivated and are then retracted to their closed, unexpanded position to, again, define with the electrode tip housing-portions 32 the unexpanded outer wall of the electrode tip 30. In this way, the patient end 26 of the catheter 2 may be easily withdrawn from the fallopian tube 24, uterine cavity and cervix by the physician.

Figure 4:
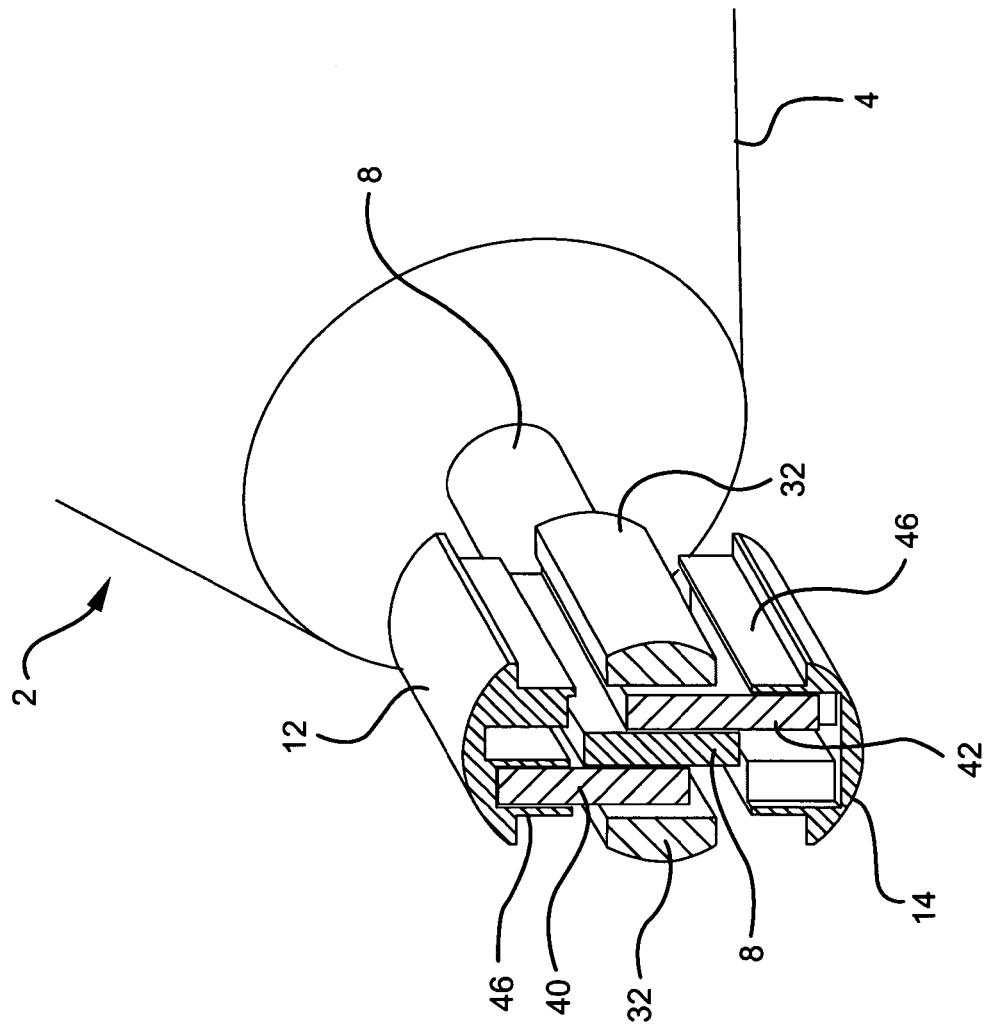
FIG. 4 is an isometric view of a cut away portion of the tubal sterilization device shown in FIG. 2.

The mechanism for expanding and retracting the electrodes 12, 14 will now be described. First, an elongated, flexible push rod 8 extends axially through the interior passageway 6 of the hollow catheter 2 from the second end 28 of the catheter 2 which is accessible by the physician to the first end 26 which is inserted transcervically into the fallopian tube 24 of the patient. The push rod 8 is axially movable by the physician in the catheter passageway 6. As shown in FIG. 4, within the electrode tip cavity 34 are situated first and second pivot arms 40, 42. Each of the first and second pivot arms 40, 42 is mounted to one or both of the electrode tip housing portions 32 by a pivot pin 44 such that the pivot arms 40, 42 pivot about the pivot pin 44 radially inwardly and outwardly.

Figure 5:
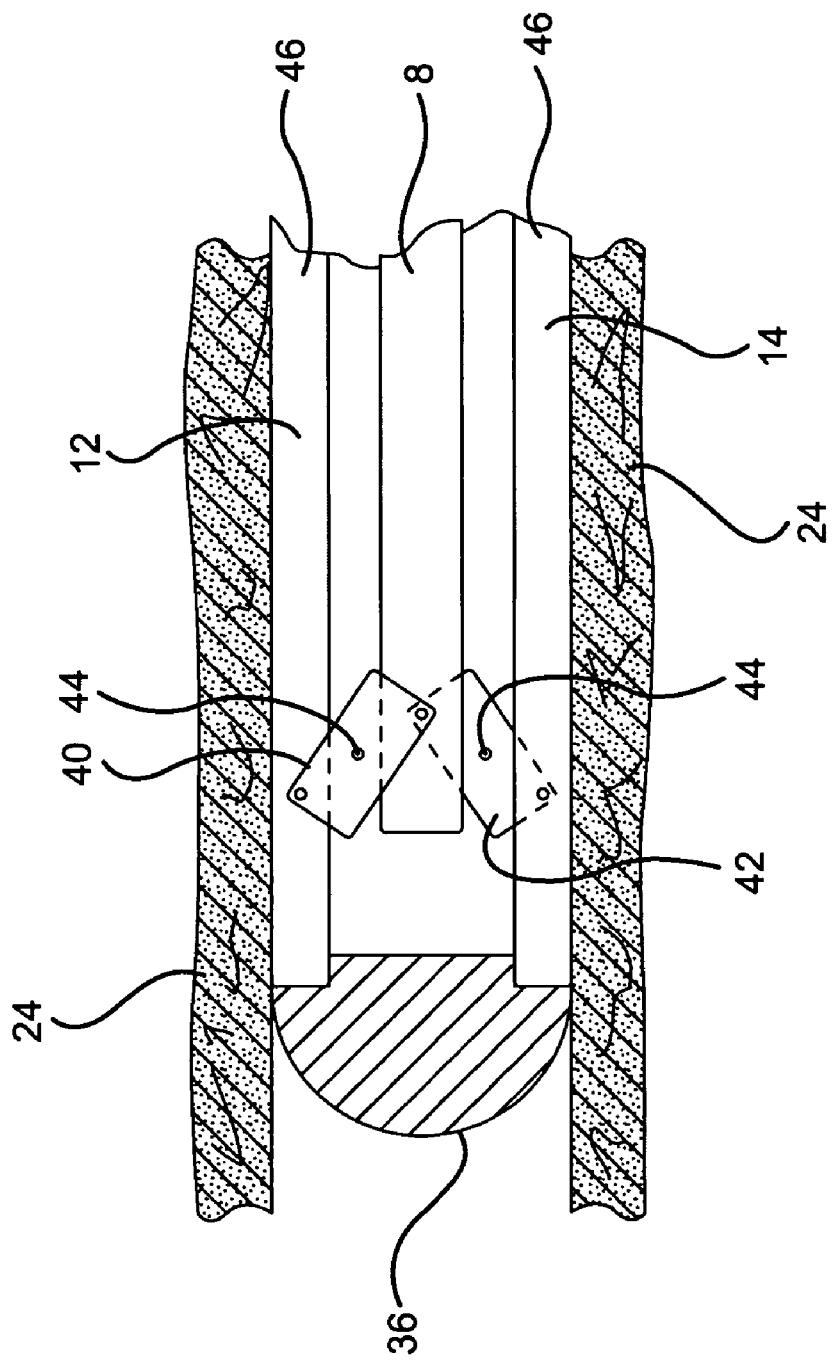
FIG. 5 is a diagrammatic cross-sectional view of a portion of the tubal sterilization device shown in FIG. 2 and illustrating the operation thereof.
Figure 6:
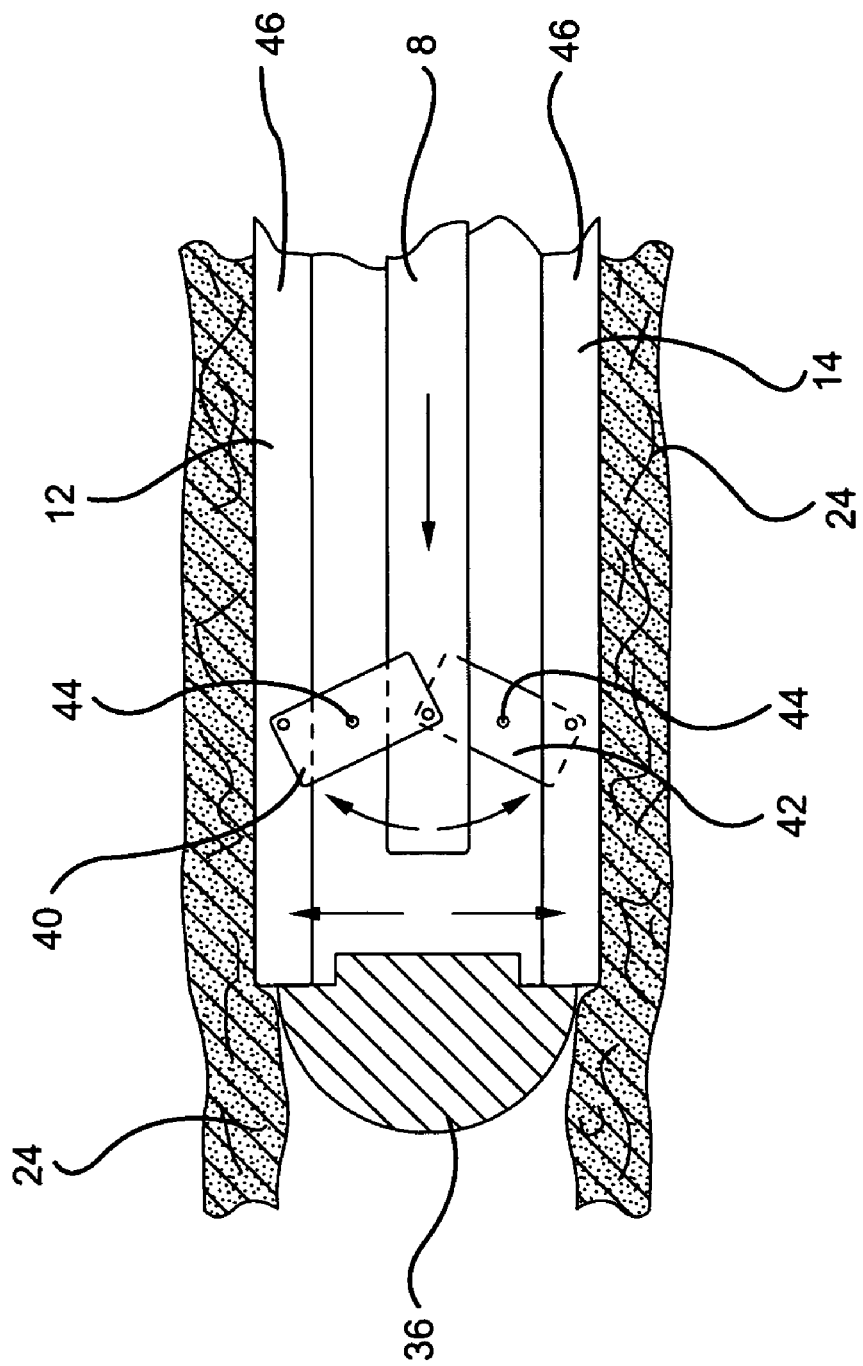
FIG. 6 is a diagrammatic cross-sectional view of a portion of the tubal sterilization device shown in FIG. 2 and further illustrating the operation thereof.
Figure 7:
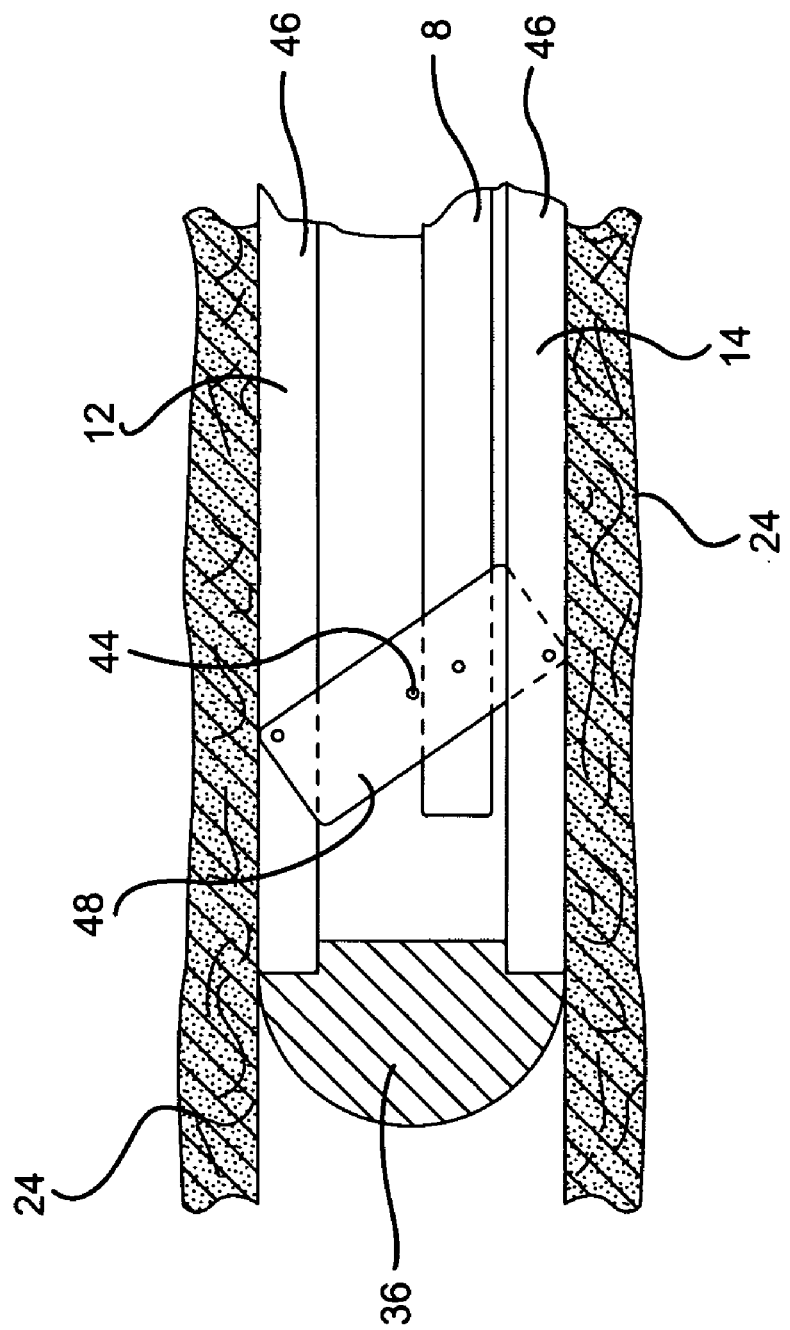
FIG. 7 is a diagrammatic cross-sectional view of a portion of the tubal sterilization device shown in FIG. 2 and illustrating an alternative version of the device.

More specifically and as shown in FIGS. 4–6, it is preferred if each pivot arm 40, 42 is in the general shape of a rectangular plate and is pivotally mounted on an opposite side of the electrode housing (i.e., the housing portions 32). The pivot arms 40, 42 are separated from each other a predetermined distance. The push rod 8 may be cylindrical for most of its length but is preferably flattened into a plate-like shape at its free end which is interposed between the first and second pivot arms 40, 42. As more clearly shown diagrammatically in FIGS. 5 and 6, each of the first and second pivot arms 40, 42 is also pivotally mounted in one corner thereof to the push rod 8 and may be pivotally mounted in a diametrically opposite corner to a corresponding one of the first and second electrodes 12, 14, each electrode having a radially inwardly extending portion 46 (see FIG. 4) for pivotal connection to its respective pivot arm 40, 42.

As shown in FIGS. 5 and 6, axial withdrawing movement of the push rod 8 will correspondingly cause radial movement of the first and second electrodes 12, 14 from the open, expanded position to the closed, unexpanded position through the pivotal movement of each of the first and second pivot arms 40, 42. Similarly, opposite insertion axial movement of the push rod 8 causes the first and second electrodes 12, 14 to move from the unexpanded position to the expanded position again through the pivoting action of the first and second pivot arms 40, 42. Thus, the physician may control the expansion and retraction of the first and second electrodes 12, 14 by respectively pushing or pulling on the push rod 8 at the second end 28 (i.e., the physician's manipulation end) of the catheter 2.

Of course, it is not necessary for the first and second pivot arms 40, 42 to be pivotally attached to the first and second electrodes 12, 14 respectively. As long as one end of each pivot arm engages a corresponding electrode, movement of the pivot arms 40, 42 will cause the electrodes 12, 14 to move from the first, unexpanded position to the second, expanded position. The fallopian tube 24 itself, because it is stretched, will exert pressure on the electrodes 12, 14 to close them if the pivot arms 40, 42 are retracted inwardly of the tip cavity 34 by the physician.

It is envisioned that only one pivot or hinge arm 48 may be used to expand and retract the first and second electrodes 12, 14. As diagrammatically shown in FIG. 7, the single hinge arm 48 may be pivotally mounted to the electrode tip housing 32, and further linked to the push rod 8 to cause the hinge arm 48 to pivot on the housing in opposite directions upon axial movement of the push rod 8. Opposite ends of the hinge arm 48 may be pivotally attached to downwardly extending protrusions 46 (see FIG. 4) of the first and second electrodes 12, 14 so that the electrodes expand and retract on the electrode tip 30 in response to pivotal movement of the hinge arm 48.

Another embodiment of the tubal sterilization device formed in accordance with the present invention is illustrated by FIGS. 8–12. This embodiment also has an expandable RF energy electrode tip, but uses a plunger 50 to selectively expand the electrodes.

Figure 8:
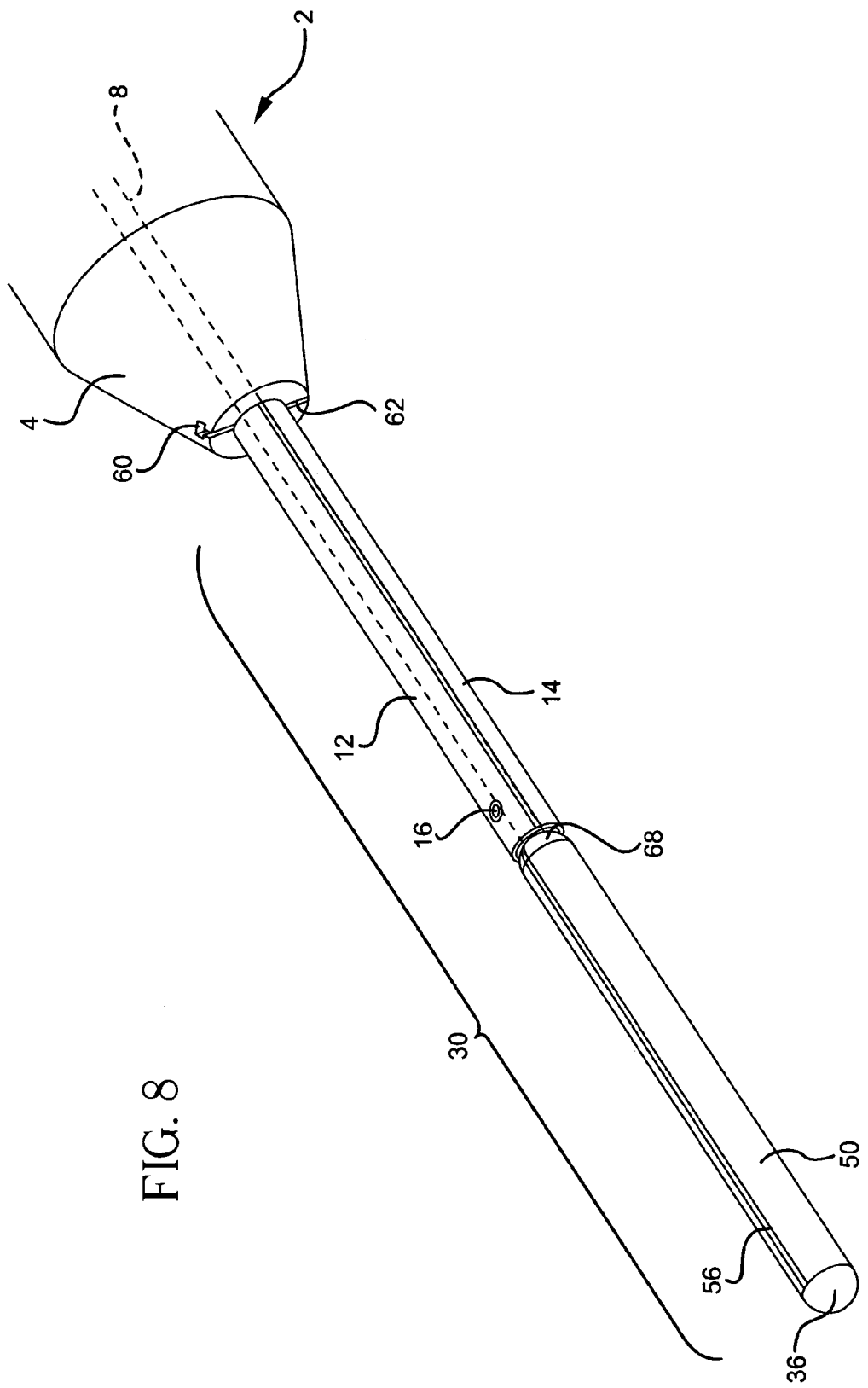
FIG. 8 is an isometric view of a tubal sterilization device formed in accordance with a second form of the present invention.
Figure 9:
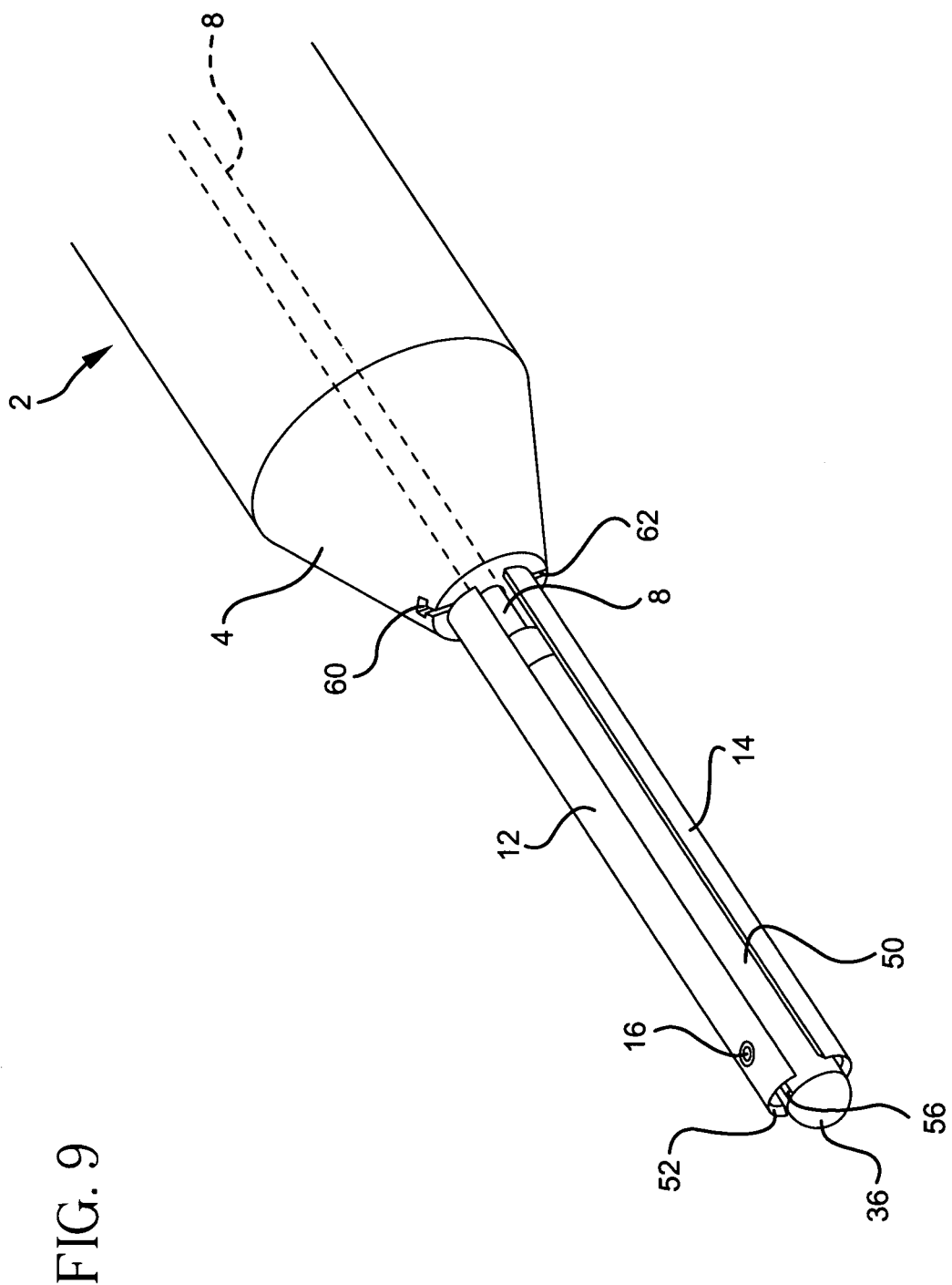
FIG. 9 is an isometric view of the tubal sterilization device shown in FIG. 8 and illustrating the operation thereof.
Figure 10:
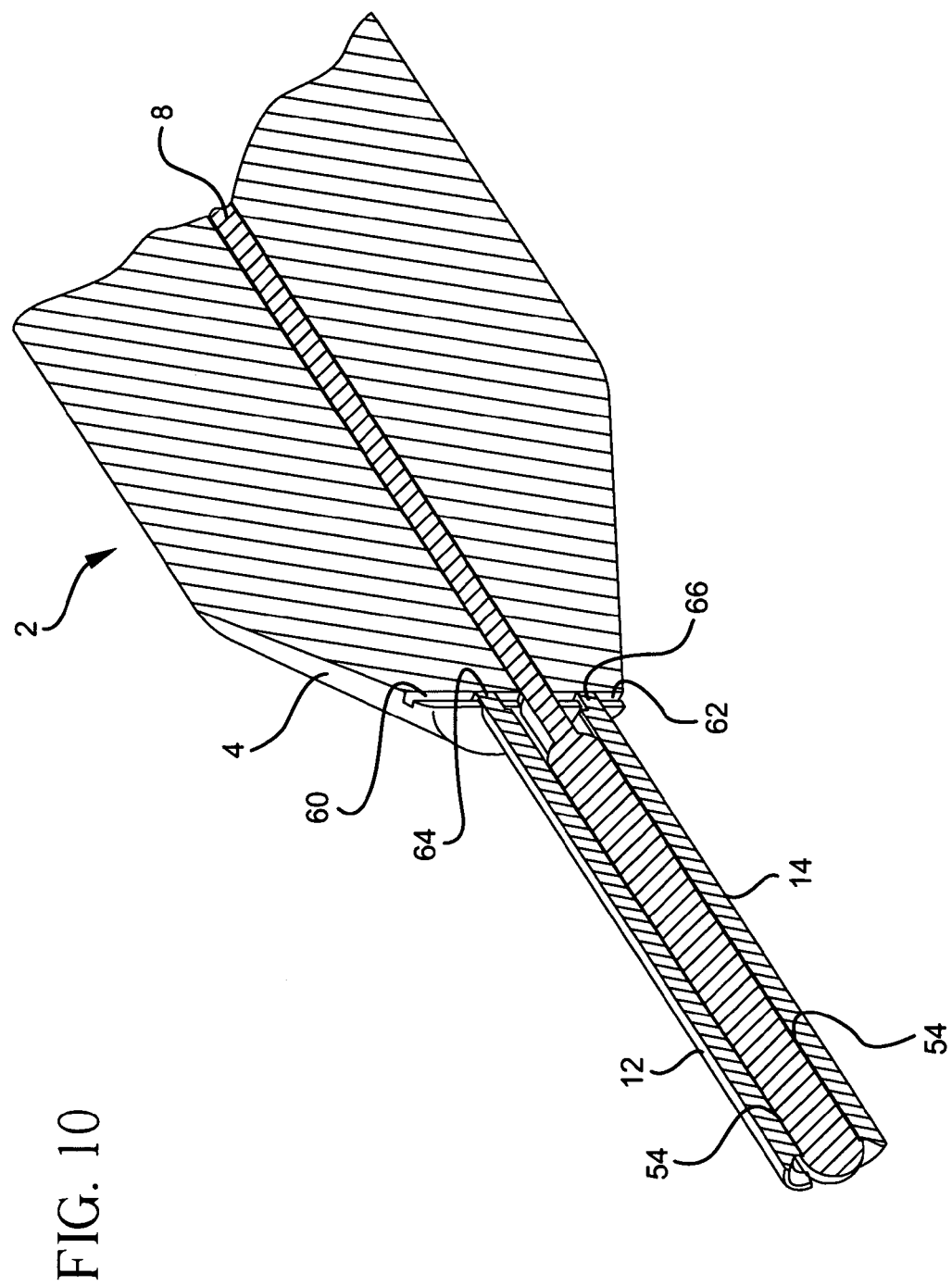
FIG. 10 is a cross-sectional view of the tubal sterilization device shown in FIG. 9, taken along line 10—10 of FIG. 9.
Figure 12:
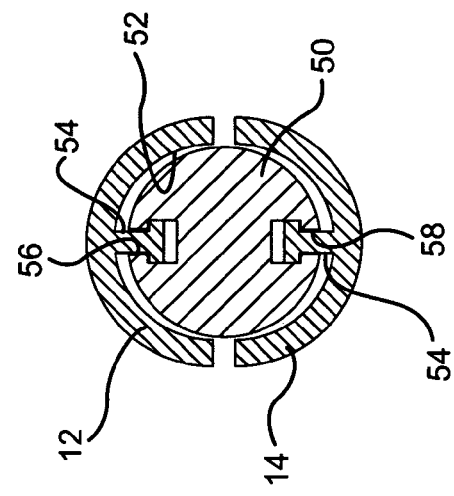
FIG. 12 is a cross-sectional view of the tubal sterilization device shown in FIG. 9, taken along line 12—12 of FIG. 9.
Figure 11:
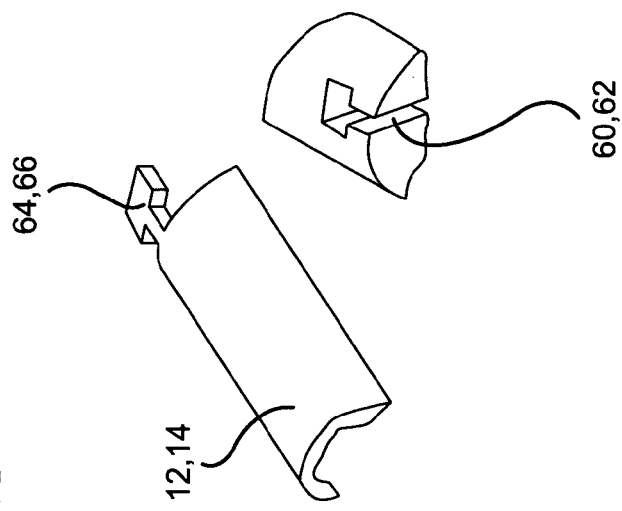
FIG. 11 is an exploded, isometric view of portions of the tubal sterilization device shown in FIG. 8.

As shown in FIGS. 8–10, the electrode tip 30, i.e., the first end 26 of the hollow catheter 2, is formed with semicircular or arcuate first and second electrodes 12, 14 situated diametrically opposite one another and movable from a closed, unexpanded state to an open, expanded state, the two electrodes 12, 14 at least partially defining the electrode tip 30 with an inner bore 52. As before, a push rod 8 extends through the catheter passageway 6 from the physician's manipulation end (i.e., the second end 28) of the catheter 2 to the distal first end 26 of the catheter (i.e., the electrode tip 30). The push rod 8 is axially movable within the passageway 6 of the catheter 2. A plunger 50 which is preferably cylindrical in shape and which includes a blunt tip end 36 to prevent perforation of the fallopian tube tissue is operatively coupled to the push rod 8. The plunger 50 preferably has a diameter which is substantially equal to the distance between the first and second electrodes 12, 14 when they reside in their expanded state. The plunger 50 is movable between a first position, where it is at least partially in non-alignment, but preferably in full non-alignment, axially with the electrodes 12, 14, and a second position, where the plunger 50 is received within the inner bore 52 of the electrode tip 30 defined at least partially by the first and second electrodes 12, 14 and in axial alignment with the first and second electrodes. Even more preferably, the plunger 50 resides in front of the axial free end of the electrode tip 30 when the patient tip 26 of the catheter 2 is maneuvered into its proper position within the fallopian tube 24 by the physician, and is retracted by the physician pulling on the push rod 8 to reside between the electrodes 12, 14, forcing them to separate and expand. The plunger 50 is movable between these positions when the push rod 8 is axially moved in opposite directions by the physician.

Stated in greater detail, when the plunger 50 is in the first position in non-alignment with the electrodes 12, 14, it extends beyond the distal axial end of the electrodes and, even more preferably, has substantially the same diameter as the electrode tip 30 at least partially defined by the electrodes 12, 14 when the electrodes are in the closed, unexpanded state. When the electrode tip 30 is in its closed, unexpanded state and the plunger 50 is in the first position in front of the electrode tip, the physician manipulates the catheter 2 through the cervix and the uterine cavity and positions the electrode tip 30 (and extending plunger 50) for placement in the intramural segment of the tubal osteum. Once the electrode tip is properly positioned, the physician partially withdraws the push rod 8. This, in turn, forces the plunger 50 to be received between the first and second electrodes 12, 14. The plunger 50, with its particular diameter, forces the two electrodes 12, 14 to separate a further distance from one another and expand to the open position as the plunger 50 is moved to its second position between and in alignment with the electrodes 12, 14. The plunger 50 preferably is formed from a non-electrically conductive material so as not to short out the electrodes 12, 14, which are provided with a bipolar RF voltage. After being properly positioned within the fallopian tube 24 and expanded to their open state, the electrodes 12, 14 are energized by providing RF energy to them to heat the surrounding tissue of the fallopian tube 24.

In the plunger embodiment shown in FIGS. 8–12, the outer wall of the electrode tip 30 may be defined by solely the first and second electrodes 12, 14 without electrode tip housing portions 32. Alternatively, as in the previously described embodiment illustrated by FIGS. 1–7, the electrode tip 30 may include opposite housing portions 32 extending axially between adjacent facing side edges of the first and second electrodes 12, 14 and which define with the electrodes the outer wall of the electrode tip 30.

Also as in the previous embodiment, the presently described embodiment of the tubal sterilization device may include a temperature sensor 16, such as a thermistor or the like, which is mounted insulatively on the one or both of the electrodes 12, 14 or on one or both of the electrode tip housing portions 32 to detect the temperature of the tissue of the fallopian tube 24 undergoing heating. The temperature sensor 16 is connected by wires 10, flexible conductive runs or the like to a control circuit 20 which, in a feedback arrangement, controls the power of the RF energy supplied to the electrodes 12, 14 by an RF signal generator 22 in the manner as described previously with respect to the first embodiment. Furthermore, each electrode 12, 14 is connected to an RF signal generator 22 by wires 10, conductive runs or the like, as described previously.

After the heating procedure is accomplished, the electrodes 12, 14 are deenergized, and the physician pushes on the push rod 8 to cause the plunger 50 to move forward to its first position in front of and in non-alignment with the electrodes 12, 14. The electrodes retract to their closed, unexpanded state so that the patient end 26 of the catheter 2 may now be withdrawn from the fallopian tube 24 by the physician.

Preferably, each of the first and second electrodes 12, 14 is axially slidably attached to the plunger 50. The purpose of this is to not only prevent the full disengagement of the electrodes from the plunger 50, but also to help prevent the electrodes 12, 14 from rotating inadvertently with respect to the plunger. More specifically, and as shown in FIGS. 9–12, each of the first and second electrodes 12, 14 has an inner facing surface, and a protrusion 54 extending outwardly from the inner facing surface and extending axially along the length of the electrode. The plunger 50, correspondingly, has an outer surface which faces the inner facing surfaces of the first and second electrodes. Additionally, the outer surface of the plunger 50 includes first and second slots 56, 58 formed therein, which slots 56, 58 extend axially along the length of the plunger 50. Like the preferred positioning of the first and second electrodes 12, 14, the first and second slots 56, 58 are positioned on the outer surface of the plunger 50 diametrically opposite one another. The protrusion 54 of the first electrode 12 is slidably received by the first slot 56, and the protrusion of the second electrode 14 is slidably received by the second slot 58. The corresponding slots and protrusions may be partially dovetail-shaped in cross-section or, more preferably, may be correspondingly T-shaped in cross-section (see FIG. 12) to ensure that each protrusion 54 remains captured by its corresponding slot 56, 58 to prevent the plunger 50 and the electrodes 12, 14 from completely separating but which also allows the electrodes 12, 14 to expand when the plunger 50 is received therebetween; that is, each T-shaped electrode protrusion 54 may move radially (with respect to the electrode tip 30) within its respective T-shaped plunger slot 56, 58.

Additionally, as mentioned previously, the catheter includes a housing or outer covering. To further ensure that the electrodes do not become separated from the catheter, the first and second electrodes 12, 14 may be radially slidably attached to the catheter housing 4.

As shown in FIGS. 8–12, the catheter housing 4 situated at the first end of the catheter 2 includes a first slot 60 and a diametrically opposed second slot 62 formed radially at least partially through the thickness of the housing 4. Additionally, the first electrode 12 has an inner situated axial end and a first protrusion 64 extending axially from this axial end. Similarly, the second electrode 14 has an inner situated axial end and a second protrusion 66 extending axially from this axial end. The first protrusion 64 is slidably received by the first slot 60 of the catheter housing 4 and the second protrusion 66 is slidably received the by second slot 62 of the catheter housing. Thus, the first and second electrodes 12, 14 are attached to the catheter housing 4 and are radially slidable with respect to the catheter housing when the first and second electrodes are moved between the first, unexpanded state and the second, expanded state. The first and second slots 60, 62 and the first and second protrusions 64, 66 may also have a dovetail shape in cross-section to ensure that the first and second protrusions remain slidably captured within the first and second slots of the catheter housing, respectively, and to ensure that the first and second electrodes 12, 14 remain attached to the catheter housing 4.

In the embodiment just described and shown in FIGS. 8–12, when the plunger 50 is moved from between the electrodes 12, 14 to at least partially in front of the electrodes, the electrodes retract to their closed, unexpanded state, to define the electrode tip 30 with its smaller diameter. The electrodes 12, 14 will collapse to their closed state under the resiliency and force of the surrounding tissue, which had been stretched when the electrodes were separated to their expanded state. However, to facilitate their retraction, the first and second electrodes 12, 14 may be formed from spring steel which, of course, has some resiliency so that the electrodes will collapse to their unexpanded state when the plunger 50 is moved from between the electrodes. To further ensure their retraction to the collapsed or closed state, the electrodes 12, 14 may be fixedly attached to the catheter housing 4, rather than being radially slidable with respect to the catheter housing. By being fixedly attached to the catheter housing 4, the electrodes 12, 14 will be tensioned even further when they are expanded by the plunger 50 being received between them, and they will return to their unexpanded state when the plunger is returned to its initial state at least partially in front of the electrodes.

Figure 13:
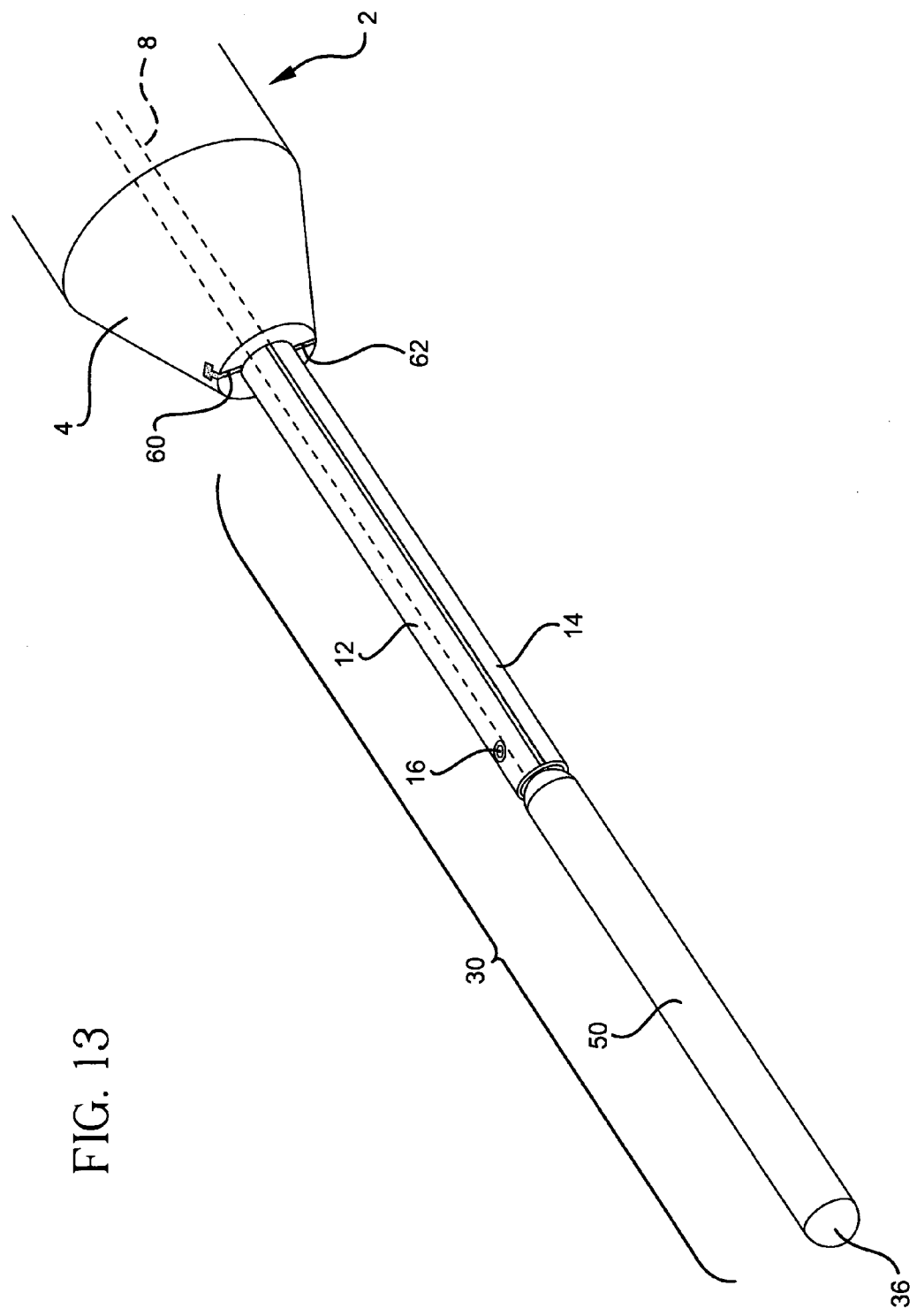
FIG. 13 is an isometric view of a tubal sterilization device formed in accordance with a third form of the present invention.
Figure 14:
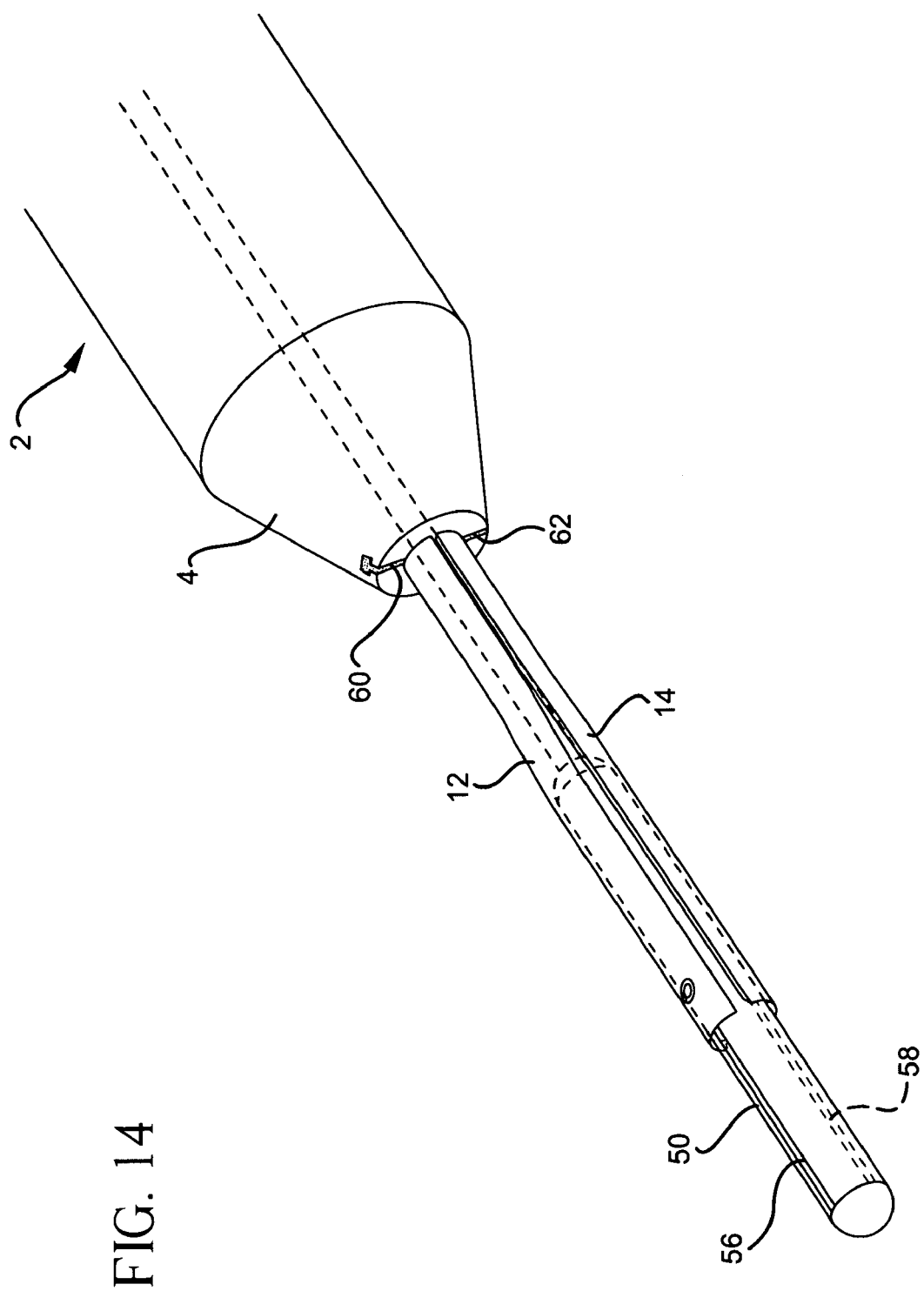
FIG. 14 is an isometric view of the tubal sterilization device shown in FIG. 13 and illustrating the operation of the device.
Figure 15:
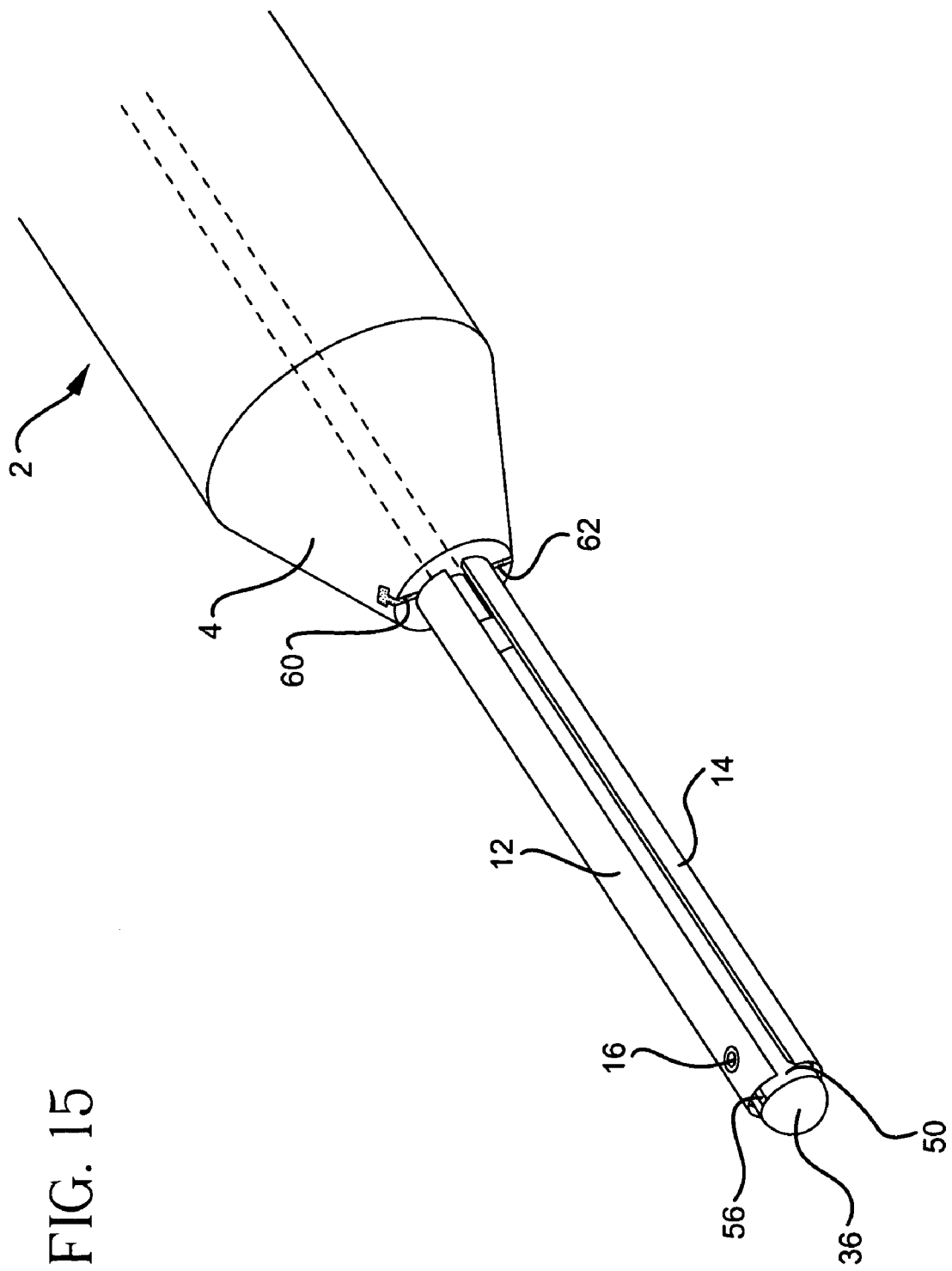
FIG. 15 is an isometric view of the tubal sterilization device shown in FIG. 13 and further illustrating the operation of the device.
Figure 16A:
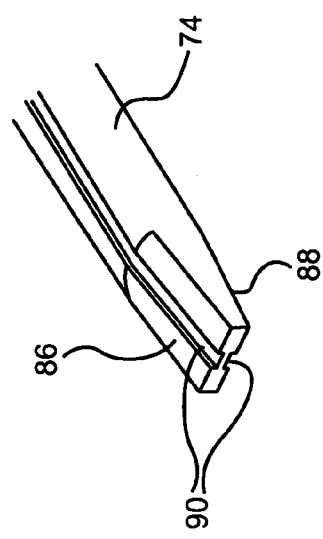
FIG. 16A is a detailed, partial isometric view of portion of the tubal sterilization device shown in FIG. 16.
Figure 16:
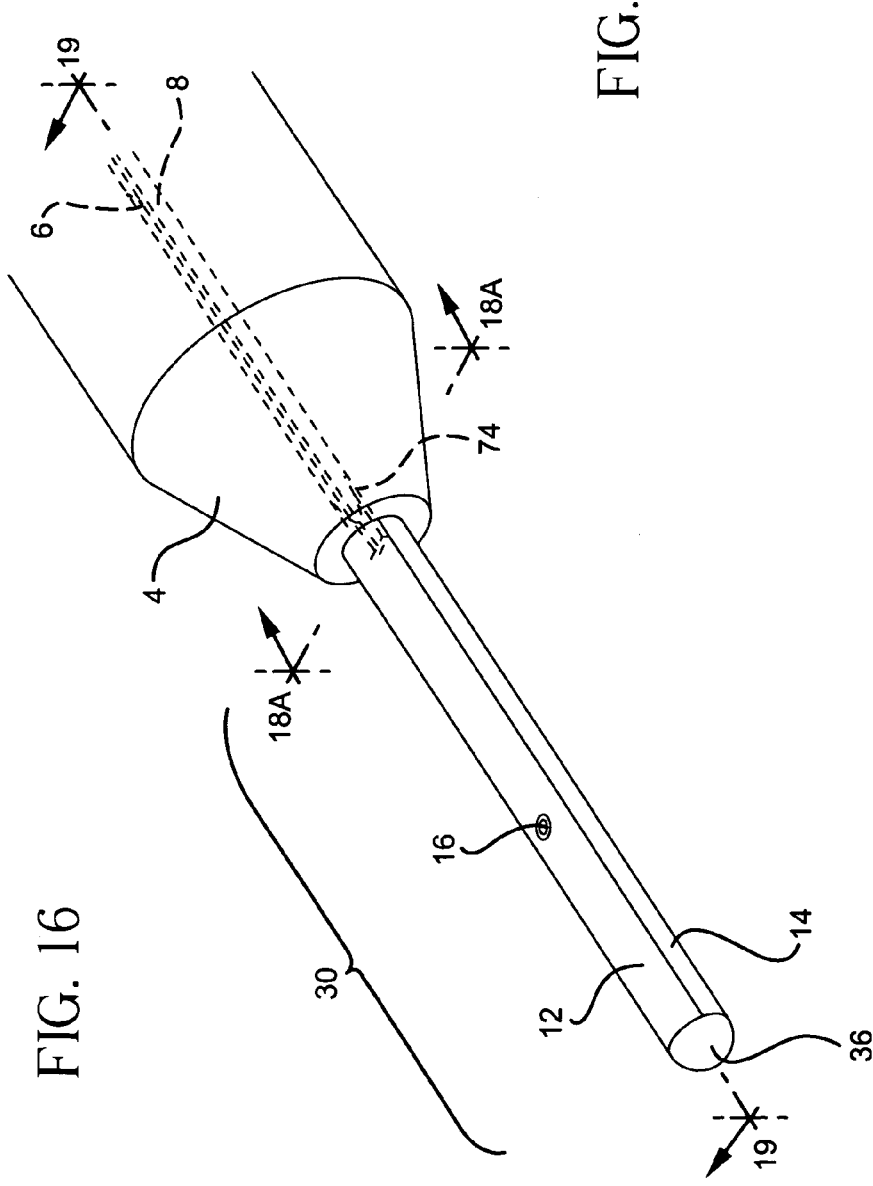
FIG. 16 is an isometric view of a tubal sterilization device formed in accordance with a fourth form of the present invention.
Figure 17:
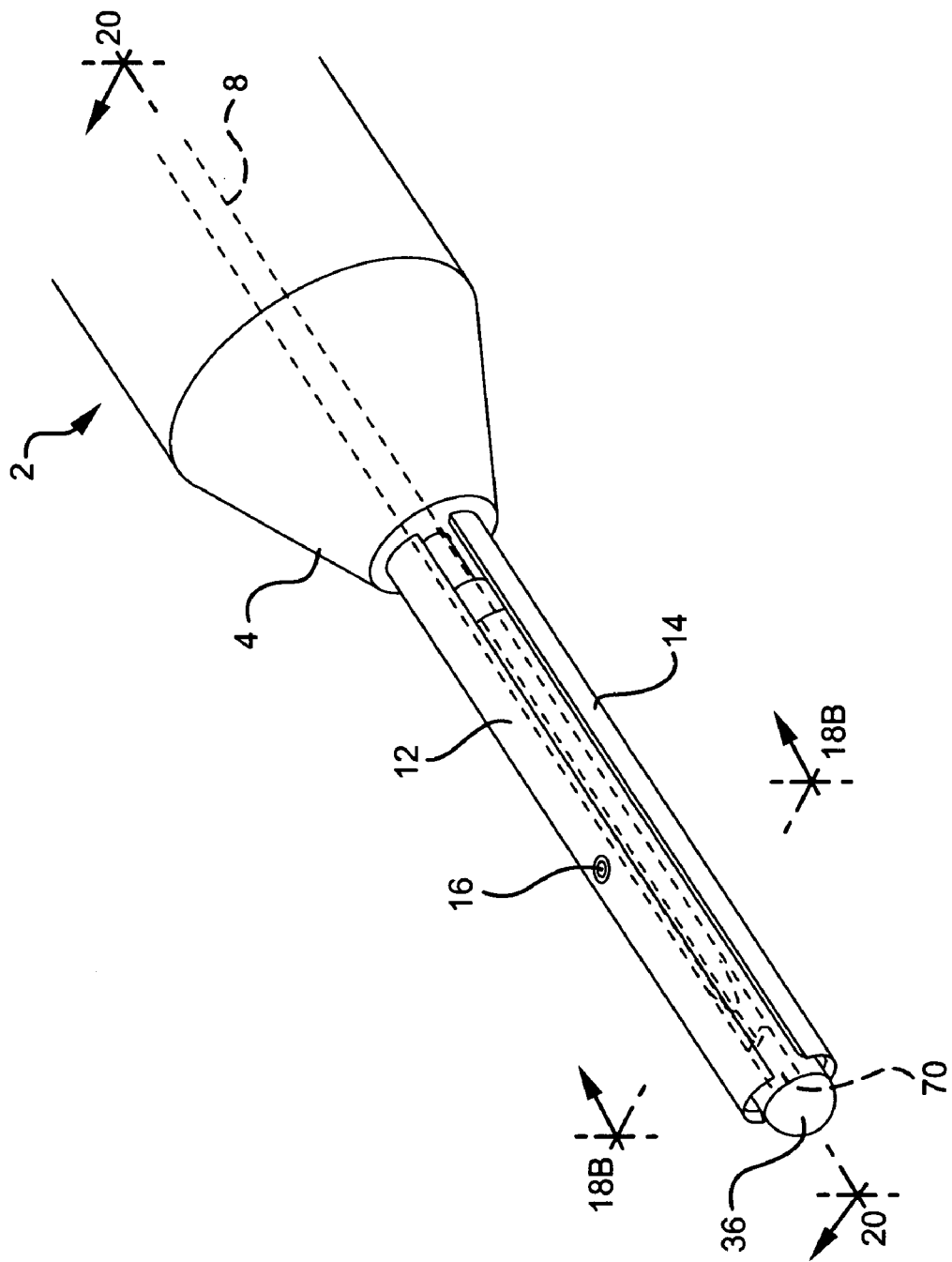
FIG. 17 is an isometric view of the tubal sterilization device shown in FIG. 16 and illustrating the operation of the device.
Figure 19:
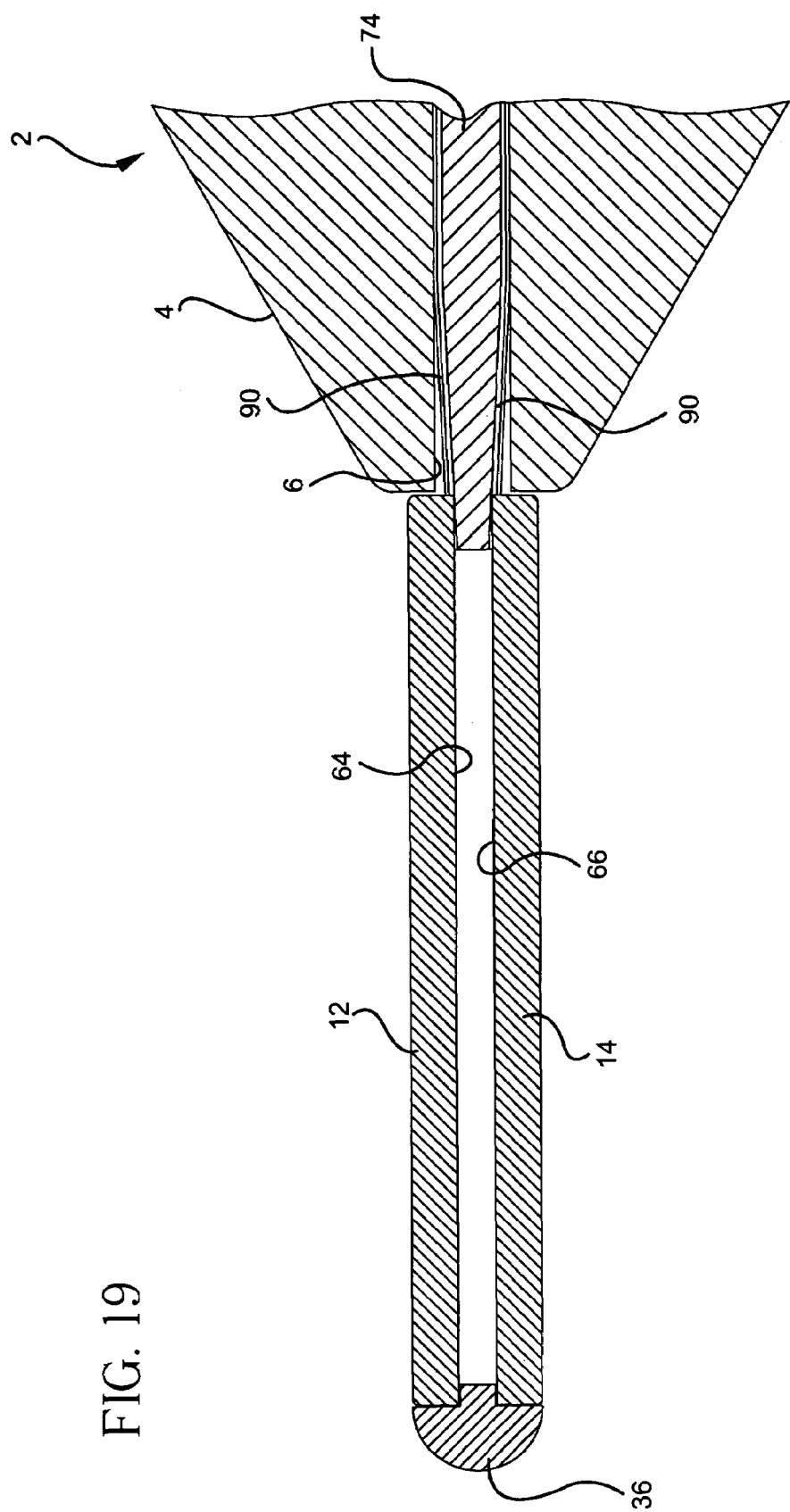
FIG. 19 is a cross-sectional view of the tubal sterilization device shown in FIG. 16, taken along line 19—19 of FIG. 16.
Figure 20:
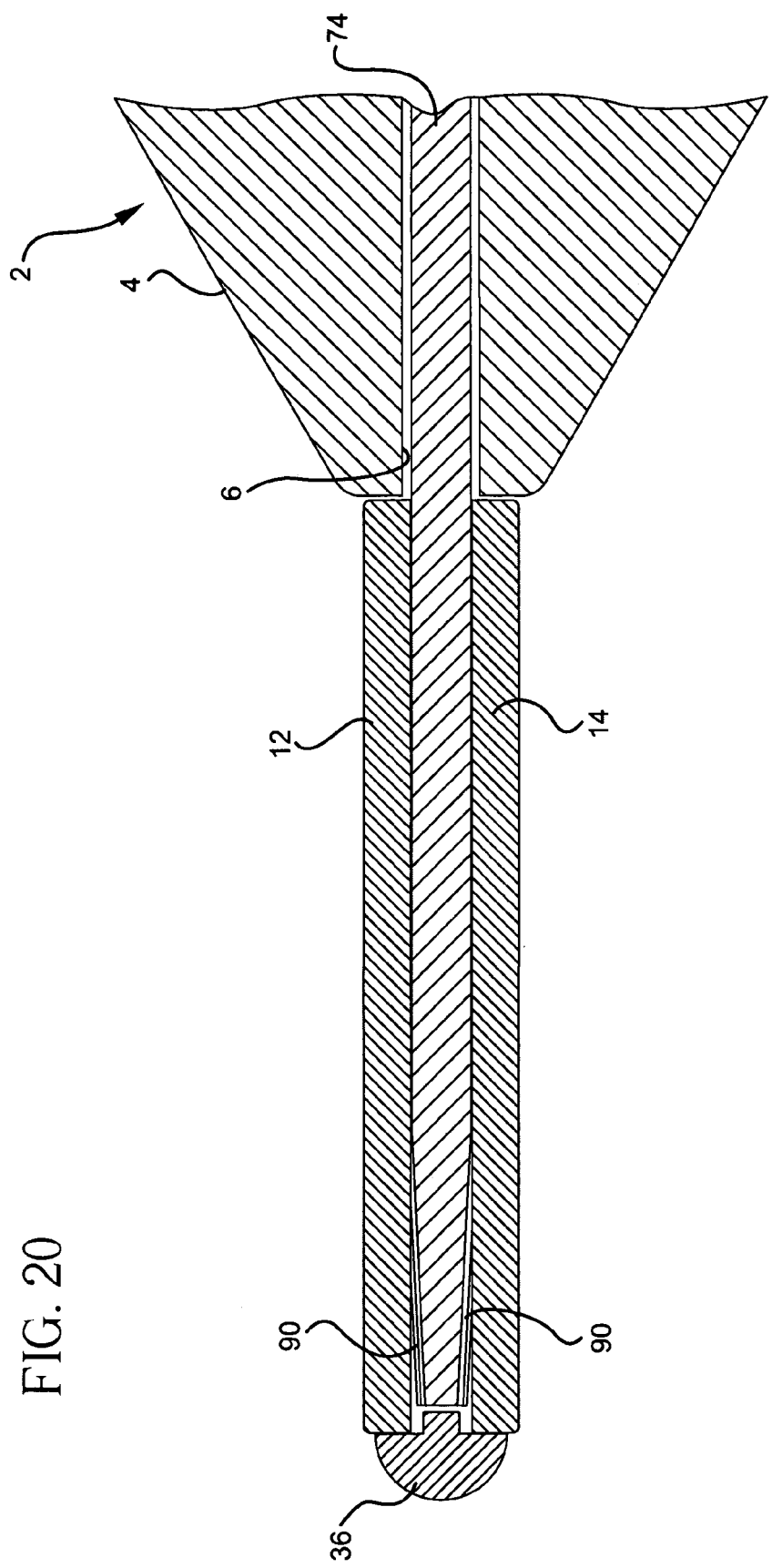
FIG. 20 is a cross-sectional view of the tubal sterilization device shown in FIG. 17, taken along line 20—20.

One way to fixedly attach the electrodes 12, 14 to the catheter housing 4 is to have the electrode protrusions 64, 66 received by the catheter housing slots 60, 62 and held immovably captive therein by having the slots filled with an epoxy or other filler so that the electrode protrusions cannot slide radially within the catheter housing slots 60, 62. The electrodes 12, 14 will then bend or deform slightly when forced to separate by the plunger 50 received between them, as illustrated by FIGS. 13–15. The resiliency of the spring steel will allow the electrodes 12, 14 to return to their initial shape when the plunger 50 is withdrawn from between them.

As mentioned previously, the plunger 50 is preferably formed to be generally cylindrical in shape. However, to facilitate its being received between the first and second electrodes 12, 14 and forcing them to separate further, the plunger 50 may have its proximal end 68 opposite the blunt tip end 36 rounded or conically-shaped with an inwardly sloping wall defining a smaller diameter at the proximal end 68. The axial free ends of the electrodes 12, 14 may also be radially beveled to help guide and accept the rounded or conically-shaped proximal end 68 of the plunger 50 between the electrodes.

A further embodiment of the tubal sterilization device formed in accordance with the present invention is illustrated by FIGS. 16–20. This embodiment may be generally referred to as a "push wedge" design.

In this particular embodiment shown in FIGS. 16–20, the first end 26 (i.e., the patient end) of the hollow catheter 2 includes a hollow barrel portion 70 which is generally circular in cross-section and defines an interior bore 72. The interior bore 72 is preferably in communication with the passageway 6 of the hollow catheter 2. A wedge-shaped piston 74 is mounted in the interior bore 72 of the barrel 70 and is axially slidable therein.

As in the other embodiments, a push rod 8 extends through the passageway 6 of the catheter 2 and is axially movable within the passageway. The wedge-shaped piston 74 in the barrel bore 72 is operatively coupled to the push rod 8 so that axial movement of the push rod causes axial movement of the wedge-shaped piston 74 within the barrel 70.

The barrel 70 has an outer surface, and correspondingly, each of the first and second electrodes 12, 14 has an inner facing surface and is mounted on the barrel 70 with its inner facing surface facing the outer surface of the barrel. Furthermore, the first and second electrodes 12, 14 are radially movable on the barrel 70 between the first, unexpanded state and the second, expanded state.

The first and second electrodes 12, 14 are arcuate or semicircular in cross-section, and preferably the radius of the inner facing surface of each electrode is equal to or slightly greater than the radius of the outer surface of the barrel 70 so that the electrodes 12, 14 conform closely to the dimensions of the barrel 70 and rest closely on the outer surface of the barrel when in the first, unexpanded state.

The first electrode 12 has a first protrusion 76 which extends outwardly of its inwardly facing surface. Similarly, the second electrode 14 includes a second protrusion 78 extending outwardly of its inner facing surface. Each of the first and second protrusions 76, 78 may be formed at its free standing end with an enlarged head portion 80 to provide each protrusion with a cross-sectional "T" shape. Again, like the other embodiments, preferably the first and second electrodes 12, 14 are diametrically situated opposite one another on the barrel 70.

The barrel 70 includes a first slot 82 formed axially at least partially along the length thereof and through the thickness of the barrel so that it communicates with the interior bore 72 of the barrel. Similarly, the barrel 70 includes a second slot 84 which is formed axially at least partially along the length of the barrel and through the thickness of the barrel and which communicates with the interior bore 72 of the barrel. The first and second slots 82, 84 are also diametrically situated opposite one another and respectively in alignment with the first and second protrusions 76, 78 of the electrodes. The first protrusion 76 of the first electrode 12 is slidably received by the first slot 82 of the barrel 70, and the second protrusion 78 of the second electrode 14 is slidably received by the second slot 84 of the barrel 70 so that at least portions of the first and second protrusions, and in particular the head portions 80 thereof, extend into the interior bore 72 of the barrel 70.

The wedge-shaped piston 74 includes at least first and second sloped camming surfaces 86, 88 formed over at least a portion thereof. The first and second camming surfaces 86, 88 are preferably formed on opposite sides of the piston 74. The first camming surface 86 selectively engages the head portion 80 of the first protrusion 76 of the first electrode, and the second camming surface 88 selectively engages the second protrusion 78 of the second electrode. Even more preferably, each of the camming surfaces 86, 88 includes a slot 90 formed therein which at least partially receives the head portion 80 of a respective protrusion of the electrodes. The slots 90 and cooperating electrode protrusions 76, 78 help prevent the piston 74 from rotating within the barrel 70 during axial movement of the piston therein.

When the wedge-shaped piston 74 moves axially within the interior bore 72 of the barrel, the head portions 80 of the first and second protrusions 76, 78 engage and ride up or down the first and second camming surfaces 86, 88, respectively, depending upon the direction of axial movement of the wedge-shaped piston within the barrel. Thus, axial movement of the wedge-shaped piston 74 within the barrel 70 causes a reciprocal radial movement of the first and second electrodes 12, 14 with respect to the barrel between the first, unexpanded state and the second, expanded state due to the engagement of the first and second protrusions 76, 78 respectively with the first and second camming surfaces 86, 88.

With this particular "push wedge" design illustrated by FIGS. 16–20, the first and second electrodes 12, 14 normally rest on the outer surface of the barrel 70 in the closed state when the physician manipulates the catheter transcervically for placement in a position preferably at the intramural segment of the tubal osteum of the fallopian tube 24. During this positioning, the head portions 80 of the first and second protrusions 76, 78 either are in non-engagement with the wedge-shaped piston 74, so that the protrusions extend to their full extent into the interior bore 72 of the barrel, with the electrodes 12, 14 resting on the outer surface of the barrel 70, or they are engaging the lowest part of their respective camming surfaces 86, 88 and are not substantially deflected thereby. Once the electrode tip 30 of the catheter is properly positioned by the physician, the physician pushes forward on the push rod 8 which correspondingly moves the wedge-shaped piston 74 axially within the barrel so that the head portions 80 of the first and second protrusions 76, 78 ride up on the first and second camming surfaces 86, 88 to separate from each other. This, in turn, causes the first and second electrodes 12, 14 to rise from the outer surface of the barrel 70 and separate from each other so that the electrode tip 30 is now in an operational, expanded state. The electrodes 12, 14 are held in place on the barrel, as the enlarged head portion 80 of each protrusion is greater in width than that of the first and second slots 82, 84 in which the corresponding protrusion is received.

Once the electrodes 12, 14 have separated, the physician energizes the electrodes by providing them with a bipolar RF voltage to heat the surrounding tissue of the fallopian tube 24. Preferably, the barrel 70 is made from a non-electrically conductive material so that it will not cause the first and second electrodes 12, 14 to short to one another.

As in the previous embodiments, a temperature sensor 16, such as a thermistor, thermocouple, thermopile or the like, may be insulatively mounted on one or both of the electrodes 12, 14 or mounted on the surface of the barrel 70 to detect the temperature of the tissue being heated. The temperature sensor 16 is connected by wires 10, conductive runs or the like through the barrel bore 72 and catheter passageway 6 to a control circuit 20, such as described previously, and provides a signal to the control circuit which is indicative of the temperature of the surrounding tissue being heated. The control circuit 20 senses and monitors the temperature sensor signal, and provides a control signal in response thereto to an RF signal generator 22, which provides the RF voltage to the electrodes 12, 14 through similarly placed wires 10, conductive runs or the like, in order to control the power of the signal provided to the electrodes in a feedback arrangement, and so as to prevent unnecessary heating or charring of the tissue of the fallopian tube 24.

After the heating step has been performed, the physician deenergizes the electrodes 12, 14, and pulls the push rod 8 in the opposite direction. The axial movement of the push rod now causes movement of the wedge-shaped piston 74 within the barrel 70 which, in turn, causes the protrusions 76, 78 to ride back down the first and second camming surfaces 86, 88 radially inwardly of the interior bore 72 of the barrel so that the first and second electrodes 12, 14 again preferably rest on the outer surface of the barrel 70 in a closed, unexpanded state. The physician may now withdraw the catheter from the fallopian tube 24 and cervix of the patient.

It should be realized throughout the description of the preferred embodiments that only two electrodes 12, 14 have been described herein. However, it is possible for the tubal sterilization device of the present invention to have a greater number of electrodes than just two, and the electrodes may be expanded and retracted in a similar manner using similar mechanisms as described in connection with the previous embodiments.

The tubal sterilization device of the present invention advantageously stretches the tissue of the fallopian tube 24 to reduce blood flow which, in turn, helps to localize the heating of the surrounding tissue. Heating is controlled by the feedback loop previously described by sensing the temperature of the tissue being heated and controlling the power of the RF signal applied to the electrodes 12, 14. The reduced diameter of the electrode tip 30 facilitates the insertion of the catheter transcervically for proper placement within the fallopian tube and allows the device to be fit into the very small opening of the tubal osteum and the intramural segment.

Furthermore, since each electrode 12, 14 is axially elongated and extends over the entire electrode tip 30, the entire surface area of the electrode is active and in contact with the tissue to be heated, and the lesion produced by heating is longer than conventional devices having axially spaced apart electrodes, such as described in U.S. Pat. No. 6,066,139, which issued to Ryan et al.

Furthermore, because each electrode 12, 14 is energized with an opposite plurality, stray currents and unintended heating is minimized.

The tubal sterilization device is flexible and easily maneuverable by a physician, and its proper positioning may be directly visualized using a hysteroscope. Furthermore, the device is inserted transcervically and obviates the need for surgery to effect sterilization.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A tubal sterilization device, which comprises:
   a hollow catheter defining an interior passageway, the catheter including a first end for insertion transcervically into a patient, and a second end opposite the first end for grasping and manipulation by a physician, at least a portion of the catheter being generally circular in cross-section and being sized for transcervical insertion into a fallopian tube of a patient; and
   at least a first electrode and a second electrode mounted on the first end of the catheter and radially movable with respect thereto between a first unexpanded position and a second expanded position, the at least first and second electrodes being spaced apart from each other a first distance when in the first unexpanded position and a second distance when in the second expanded position, the second distance being greater than the first distance, the at least first and second electrodes being responsive to RF (radio frequency) energy to cause heating of at least a portion of the fallopian tube contacting the at least first and second electrodes when the first end of the catheter is received thereby.

2. A tubal sterilization device as defined by claim 1, which further comprises means for moving the at least first and second electrodes between the first unexpanded position and the second expanded position.

3. A tubal sterilization device as defined by claim 2, wherein the means for moving the at least first and second electrodes includes at least one pivot arm, and a push rod extending through the catheter passageway and axially movable therein, the push rod being operatively connected to the at least one pivot arm, the first end of the catheter having an electrode housing, the at least first and second electrodes being movable with respect to the electrode housing, the at least one pivot arm engaging the at least first and second electrodes and causing the at least first and second electrodes to move from the first unexpanded position to the second expanded position upon axial movement of the push rod.

4. A tubal sterilization device as defined by claim 2, wherein the means for moving the at least first and second electrodes includes at least a first pivot arm and a second pivot arm, and a push rod extending through the catheter passageway and axially movable therein, the push rod being operatively connected to the at least first pivot arm and the second pivot arm, the first end of the catheter having an electrode housing, the at least first and second electrodes being movable with respect to the electrode housing, the at least first and second pivot arms being pivotally mounted to the electrode housing, the first pivot arm of the at least first and second pivot arms being pivotally mounted to the first electrode of the at least first and second electrodes, and the second pivot arm of the at least first and second pivot arms being pivotally mounted to the second electrode of the at least first and second electrodes, the at least first and second pivot arms causing the at least first and second electrodes to move between the first unexpanded position and the second expanded position upon axial movement of the push rod.

5. A tubal sterilization device as defined by claim 2, wherein the means for moving the at least first and second electrodes includes at least a first pivot arm and a second pivot arm, and a push rod extending through the catheter passageway and axially movable therein and operatively connected to the at least first and second pivot arms, the first end of the catheter having an electrode housing, the at least first and second electrodes being movable with respect to the electrode housing, the first pivot arm and the second pivot arm of the at least first and pivot arms respectively engaging the first electrode and the second electrode of the at least first and second electrodes to cause the at least first and second electrodes to move from the first unexpanded position to the second expanded position upon axial movement of the push rod.

6. A tubal sterilization device as defined by claim 2, wherein the means for moving the at least first and second electrodes includes a plunger, and a push rod extending through the catheter passageway and axially movable therein, the push rod being operatively connected to the plunger, the plunger being axially movable with respect to the at least first and second electrodes and having a transverse width which is substantially equal to the first distance which the at least first and second electrodes are spaced apart when in the second expanded position, the plunger being axially movable between a first position wherein the plunger is at least partially in non-alignment axially with the at least first and second electrodes, and a second position wherein the plunger is axially aligned with and resides between the at least first and second electrodes, the plunger being movable between the first position, wherein the at least first and second electrodes are in the first unexpanded position, and the second position, wherein the plunger exerts a radial force on the at least first and second electrodes to cause the at least first and second electrodes to move to the second expanded position upon axial movement of the push rod.

7. A tubal sterilization device as defined by claim 6, wherein each electrode of the at least first and second electrodes is axially slidably attached to the plunger.

8. A tubal sterilization device as defined by claim 7, wherein each electrode of the at least first and second electrodes includes an inner facing surface and a protrusion extending outwardly from the inner facing surface and extending axially along at least a portion of the length of the electrode; and wherein the plunger has an outer surface facing the inner facing surfaces of the at least first and second electrodes, the outer surface of the plunger having at least first and second slots formed therein and extending axially along at least a portion of the length of the plunger, the first slot and the second slot of the at least first and second slots respectively receiving the protrusion of the first electrode and the protrusion of the second electrode of the at least first and second electrodes to thereby slidably attach the at least first and second electrodes to the plunger and to prevent the at least first and second electrodes from rotating relative to the plunger.

9. A tubal sterilization device as defined by claim 6, wherein the catheter includes an outer housing; and wherein each electrode of the first and second electrodes is radially slidably attached to the catheter housing.

10. A tubal sterilization device as defined by claim 9, wherein the catheter housing includes at least a first slot and a second slot formed radially at least partially through the thickness thereof; and wherein the first electrode of the at least first and second electrodes has an axial end and a first protrusion extending axially from the axial end thereof; and wherein the second electrode of the at least first and second electrodes has an axial end and a second protrusion extending axially from the axial end thereof, the first protrusion being slidably received by the first slot of the catheter housing and the second protrusion being slidably received by the second slot of the catheter housing such that the at least first and second electrodes are attached to the catheter housing and radially slidable with respect thereto when the at least first and second electrodes move between the first unexpanded position and the second expanded position.

11. A tubal sterilization device as defined by claim 6, wherein the catheter includes an outer housing; wherein each electrode of the at least first and second electrodes includes an axial end fixedly mounted on the catheter housing; and wherein each electrode of the first and second electrodes is formed of a resilient, electrically conductive material, whereby the resiliency of the material of the at least first and second electrodes causes movement of the at least first and second electrodes from the second expanded position to the first unexpanded position when the plunger is moved by the push rod from the second position to the first position.

12. A tubal sterilization device as defined by claim 11, wherein the at least first and second electrodes are formed from resilient spring steel.

13. A tubal sterilization device as defined by claim 2, which further comprises a hollow barrel portion, the hollow barrel portion being generally circular in cross-section and defining an interior bore, the interior bore being in communication with the passageway of the catheter;
  a piston mounted in the interior bore of the barrel and axially slidable therein; and
  a push rod extending through the passageway of the catheter and axially movable therein, the piston being operatively coupled to the push rod such that axial movement of the push rod causes axial movement of the piston within the barrel, the barrel having an outer surface, each electrode of the at least first and second electrodes having an inner facing surface and being mounted on the barrel with the inner facing surface facing the outer surface of the barrel and being radially movable on the barrel between the first unexpanded position and the second expanded position, the first electrode of the at least first and second electrodes having a first protrusion extending outwardly of the inner facing surface thereof, the second electrode of the at least first and second electrodes having a second protrusion extending outwardly of the inner facing surface thereof, the barrel having at least first and second slots formed axially at least partially along the length thereof and through the thickness thereof and communicating with the interior bore of the barrel, the at least first and second protrusions being respectively received by the at least first and second slots of the barrel such that portions of the at least first and second protrusions extend into the interior bore of the barrel;

the piston having at least first and second sloped camming surfaces formed over at least a portion thereof, the first camming surface of the at least first and second camming surfaces engaging the first protrusion of the at least first and second protrusions, the second camming surface of the at least first and second camming surfaces engaging the second protrusion of the at least first and second protrusions, wherein axial movement of the piston within the barrel causes a reciprocal radial movement of the at least first and second electrodes with respect to the barrel between the first unexpanded position and the second expanded position due to the engagement of the at least first and second protrusions respectively with the at least first and second camming surfaces.

14. A tubal sterilization device as defined by claim 1, which further comprises:

an RF signal generator, the RF signal generator generating RF energy and providing the RF energy to the at least first and second electrodes.

15. A tubal sterilization device as defined by claim 14, which further comprises:

a power control circuit; and a temperature sensor, the temperature sensor being mounted on the first end of the catheter, the temperature sensor sensing the temperature of the portion of the fallopian tube being heated and providing a signal indicative thereof, the power control circuit being responsive to the signal from the temperature sensor and, in response thereto, generating a control signal, the RF signal generator being responsive to the control signal of the power control circuit and adjusting the power of the RF energy provided to the at least first and second electrodes in response thereto.

16. A method of applying heat by using RF (radio frequency) energy to a portion of a fallopian tube of a patient to cause the occlusion of the fallopian tube, which comprises the steps of:

inserting transcervically into the fallopian tube of the patient a first end of a hollow catheter defining an interior passageway, the first end of the catheter including at least a first electrode and a second electrode mounted thereon and radially movable with respect thereto between a first unexpanded position and a second expanded position, the at least first and second electrodes being spaced apart from each other a first distance when in the first unexpanded position and a second distance when in the second expanded position, the second distance being greater than the first distance;

causing the at least first and second electrodes to move from the first unexpanded position to the second expanded position to contact a portion of the fallopian tube; and applying RF energy to the at least first and second electrodes, thereby heating at least a portion of the fallopian tube contacting the at least first and second electrodes when the first and second electrodes are in the second expanded position.

17. A method as defined by claim 16, which comprises the further steps of:

sensing the temperature of the at least a portion of the fallopian tube being heated and providing an electrical signal indicative of the temperature thereof; and controlling the power of the RF energy provided to the at least first and second electrodes in response to the signal indicative of the sensed temperature.

* * * * *